(12) United States Patent
Ferber

(10) Patent No.: US 11,083,418 B2
(45) Date of Patent: Aug. 10, 2021

(54) PATIENT VISUALIZATION SYSTEM

(71) Applicant: Wellsense, Inc., Birmingham, MI (US)

(72) Inventor: Roman S. Ferber, West Bloomfield, MI (US)

(73) Assignee: Wellsense, Inc., Birmingham, MI (US)

( * ) Notice: Subject to any disclaimer, the term of this patent is extended or adjusted under 35 U.S.C. 154(b) by 932 days.

(21) Appl. No.: 15/343,808

(22) Filed: Nov. 4, 2016

(65) Prior Publication Data

US 2018/0125412 A1 May 10, 2018

(51) Int. Cl.
*A61B 5/00* (2006.01)
*A61B 5/11* (2006.01)
*A61G 7/057* (2006.01)
*A61B 5/103* (2006.01)

(52) U.S. Cl.
CPC .............. *A61B 5/743* (2013.01); *A61B 5/002* (2013.01); *A61B 5/1113* (2013.01); *A61B 5/447* (2013.01); *A61B 5/7435* (2013.01); *A61G 7/057* (2013.01); *A61B 5/1036* (2013.01); *A61B 5/6892* (2013.01); *A61B 5/746* (2013.01); *A61B 2562/0247* (2013.01); *A61B 2562/046* (2013.01)

(58) Field of Classification Search
CPC ....... A61B 5/743; A61B 5/002; A61B 5/1113; A61B 5/1036; A61B 5/447; A61B 5/6892; A61B 5/746; A61B 5/1115; A61B 5/742; A61B 5/7435; A61B 2562/0247; A61B 2562/046; A61G 7/057
See application file for complete search history.

(56) References Cited

U.S. PATENT DOCUMENTS

| | | | |
|---|---|---|---|
| 4,503,286 A | 3/1985 | Kubo et al. |
| 4,526,043 A | 7/1985 | Boie et al. |
| 4,554,930 A | 11/1985 | Kress |
| 4,758,815 A | 7/1988 | Lovell |
| 4,795,998 A | 1/1989 | Dunber et al. |
| 4,827,763 A | 5/1989 | Bourland et al. |
| 4,929,803 A | 5/1990 | Yoshida et al. |

(Continued)

FOREIGN PATENT DOCUMENTS

| | | |
|---|---|---|
| CN | 101109769 A | 1/2008 |
| DE | 3227550 A1 | 1/1983 |

(Continued)

OTHER PUBLICATIONS

Non-Final Office Action from U.S. Appl. No. 15/343,747, dated Feb. 8, 2019, 38 pages.

(Continued)

*Primary Examiner* — Devin B Henson
(74) *Attorney, Agent, or Firm* — Brooks Kushman, P.C.

(57) ABSTRACT

A patient visualization system having a processor, communicatively coupled to a pressure sensor device to periodically receive pressure sensor data experienced by a subject at locations on the pressure sensor device. The processor programmed to receive input indicative of an intervention resulting in a pressure lowering of a body area of the subject during a first high-pressure situation at a first time; and responsive to determining a second high-pressure situation at the body area of the subject at a second time later than the first time, display an indication of the input of the intervention in connection with the first high-pressure situation.

23 Claims, 24 Drawing Sheets

(56) References Cited

U.S. PATENT DOCUMENTS

| | | |
|---|---|---|
| 5,010,772 A | 4/1991 | Bourland et al. |
| 5,030,508 A | 7/1991 | Kuhn et al. |
| 5,033,291 A | 7/1991 | Podoloff et al. |
| 5,086,652 A | 2/1992 | Kropp |
| 5,102,727 A | 4/1992 | Pittman et al. |
| 5,131,259 A | 7/1992 | Kropp |
| 5,162,135 A | 11/1992 | Gregory et al. |
| 5,253,656 A | 10/1993 | Rincoe et al. |
| 5,276,432 A | 1/1994 | Travis |
| 5,505,072 A | 4/1996 | Oreper |
| 5,571,973 A | 11/1996 | Taylot |
| 5,642,096 A | 6/1997 | Leyerer et al. |
| 5,656,785 A | 8/1997 | Trainor et al. |
| 5,720,892 A | 2/1998 | Deangelis et al. |
| 5,756,904 A | 5/1998 | Oreper et al. |
| 5,808,552 A | 9/1998 | Wiley et al. |
| 5,856,644 A | 1/1999 | Burgess |
| 5,873,137 A | 2/1999 | Yavets-Chen |
| 5,905,209 A | 5/1999 | Oreper |
| 5,942,733 A | 8/1999 | Allen et al. |
| 5,970,789 A | 10/1999 | Meyer et al. |
| 5,993,400 A | 11/1999 | Rincoe et al. |
| 6,014,346 A | 1/2000 | Malone |
| 6,032,121 A | 2/2000 | Dietrich et al. |
| 6,032,542 A | 3/2000 | Warnick et al. |
| 6,067,019 A | 5/2000 | Scott |
| 6,155,120 A | 12/2000 | Taylor |
| 6,216,545 B1 | 4/2001 | Taylor |
| 6,216,546 B1 | 4/2001 | Bahr |
| 6,225,814 B1 | 5/2001 | Oreper et al. |
| 6,244,272 B1 | 6/2001 | Montant et al. |
| 6,287,253 B1 | 9/2001 | Ortega et al. |
| 6,360,598 B1 | 3/2002 | Calame et al. |
| 6,367,106 B1 | 4/2002 | Gronsman |
| 6,386,051 B1 | 5/2002 | Yoshimi et al. |
| 6,417,777 B2 | 7/2002 | Fitzgerald et al. |
| 6,432,737 B1 | 8/2002 | Webster |
| 6,438,776 B2 | 8/2002 | Ferrand et al. |
| 6,441,742 B1 | 8/2002 | Lovely et al. |
| 6,543,299 B2 | 4/2003 | Taylor |
| 6,546,813 B2 | 4/2003 | Hubbard, Jr. |
| 6,721,980 B1 | 4/2004 | Price et al. |
| 6,735,630 B1 | 5/2004 | Gelvin et al. |
| 6,897,781 B2 | 5/2005 | Cooper et al. |
| 6,945,115 B1 | 9/2005 | Wang |
| 6,964,205 B2 | 11/2005 | Papakostas et al. |
| 6,987,232 B2 | 1/2006 | Smith et al. |
| 6,993,954 B1 | 2/2006 | George et al. |
| 7,030,764 B2 | 4/2006 | Smith et al. |
| 7,090,647 B2 | 8/2006 | Mimura et al. |
| 7,119,696 B2 | 10/2006 | Borugian |
| 7,201,063 B2 | 4/2007 | Taylor |
| 7,258,026 B2 | 8/2007 | Papakostas et al. |
| 7,304,580 B2 | 12/2007 | Sullivan et al. |
| 7,319,386 B2 | 1/2008 | Collins, Jr. et al. |
| 7,330,127 B2 | 2/2008 | Price et al. |
| 7,377,133 B2 | 5/2008 | Sandbach et al. |
| 7,378,975 B1 | 5/2008 | Smith et al. |
| 7,464,605 B2 | 12/2008 | Douglas et al. |
| 7,480,951 B2 | 1/2009 | Weismiller et al. |
| 7,531,203 B2 | 5/2009 | Tao et al. |
| 7,557,718 B2 | 7/2009 | Petrosenko et al. |
| 7,559,106 B1 | 7/2009 | Crousore et al. |
| 7,568,246 B2 | 8/2009 | Weismiller et al. |
| 7,591,165 B2 | 9/2009 | Papakostas et al. |
| 7,629,890 B2 | 12/2009 | Sullivan et al. |
| 7,652,581 B2 | 1/2010 | Gentry et al. |
| 7,656,299 B2 | 2/2010 | Gentry et al. |
| 7,714,238 B2 | 5/2010 | Skinner et al. |
| 7,746,218 B2 | 6/2010 | Collins, Jr. et al. |
| 7,752,926 B2 | 7/2010 | Caminade et al. |
| 7,825,814 B2 | 11/2010 | Lokhorst et al. |
| 7,849,545 B2 | 12/2010 | Flocard et al. |
| 7,852,208 B2 | 12/2010 | Collins, Jr. et al. |
| 7,868,740 B2 | 1/2011 | McNeely et al. |
| 8,011,041 B2 | 9/2011 | Hann |
| 8,117,701 B2 | 2/2012 | Bobey et al. |
| 8,121,800 B2 | 2/2012 | Altman et al. |
| 8,258,963 B2 | 9/2012 | Dixon et al. |
| 8,272,276 B2 | 9/2012 | Gorjanc et al. |
| 8,413,271 B2 | 4/2013 | Blanchard et al. |
| 9,047,750 B2 | 6/2015 | Tamez |
| 9,179,863 B2 | 11/2015 | Brauers et al. |
| 9,295,600 B2 | 3/2016 | Receveur |
| 9,659,322 B2 | 5/2017 | Gorjanc et al. |
| 10,076,281 B2 | 9/2018 | Berezhnyy et al. |
| 2002/0013538 A1 | 1/2002 | Teller |
| 2002/0034166 A1 | 3/2002 | Barany et al. |
| 2002/0121146 A1 | 9/2002 | Manaresi et al. |
| 2003/0105389 A1 | 6/2003 | Noonan et al. |
| 2004/0046668 A1 | 3/2004 | Smith et al. |
| 2004/0059199 A1 | 3/2004 | Thomas et al. |
| 2005/0076715 A1 | 4/2005 | Kuklis et al. |
| 2005/0165284 A1 | 7/2005 | Gefen |
| 2006/0028350 A1 | 2/2006 | Bhai |
| 2006/0065060 A1 | 3/2006 | Ito et al. |
| 2006/0092133 A1 | 5/2006 | Touma et al. |
| 2006/0152378 A1 | 7/2006 | Lokhorst et al. |
| 2006/0213286 A1 | 9/2006 | De Arenaza |
| 2006/0293613 A1 | 12/2006 | Fatehi et al. |
| 2007/0008156 A1 | 1/2007 | Ueda et al. |
| 2007/0234825 A1 | 10/2007 | Loomis et al. |
| 2007/0235231 A1 | 10/2007 | Loomis et al. |
| 2008/0009686 A1 | 1/2008 | Heindrich |
| 2008/0060138 A1 | 3/2008 | Price et al. |
| 2008/0078030 A1 | 4/2008 | Lee et al. |
| 2008/0169931 A1 | 7/2008 | Gentry et al. |
| 2008/0183048 A1 | 7/2008 | Zhang |
| 2008/0186189 A1 | 8/2008 | Azzaro et al. |
| 2008/0202251 A1 | 8/2008 | Serban |
| 2008/0272918 A1 | 11/2008 | Ingersoll |
| 2008/0275326 A1 | 11/2008 | Kasielke et al. |
| 2008/0318483 A1 | 12/2008 | Salitsky et al. |
| 2009/0044334 A1 | 2/2009 | Parsell et al. |
| 2009/0048074 A1 | 2/2009 | Kamins |
| 2009/0069727 A1 | 3/2009 | Neustaedter et al. |
| 2009/0070939 A1 | 3/2009 | Hann |
| 2009/0099480 A1 | 4/2009 | Salgo et al. |
| 2009/0119843 A1 | 5/2009 | Rodgers et al. |
| 2009/0129031 A1 | 5/2009 | Someya et al. |
| 2009/0129556 A1 | 5/2009 | Ahn |
| 2009/0216466 A1 | 8/2009 | Altman et al. |
| 2009/0256817 A1 | 10/2009 | Perlin et al. |
| 2009/0289800 A1 | 11/2009 | Hansen |
| 2010/0052917 A1 | 3/2010 | Sullivan et al. |
| 2010/0162832 A1 | 7/2010 | Brauers |
| 2010/0163283 A1 | 7/2010 | Hamedi et al. |
| 2010/0268122 A1 | 10/2010 | Drennan et al. |
| 2010/0298742 A1 | 11/2010 | Perlman et al. |
| 2010/0308846 A1 | 12/2010 | Camus |
| 2011/0001622 A1 | 1/2011 | Gentry et al. |
| 2011/0030141 A1 | 2/2011 | Soderberg et al. |
| 2011/0035057 A1 | 2/2011 | Receveur et al. |
| 2011/0046498 A1 | 2/2011 | Klap |
| 2011/0068932 A1 | 3/2011 | Flocard et al. |
| 2011/0156915 A1 | 6/2011 | Brauers et al. |
| 2011/0234408 A1 | 9/2011 | Dixon et al. |
| 2011/0263950 A1 | 10/2011 | Larson |
| 2011/0264007 A1 | 10/2011 | Meyers |
| 2011/0301432 A1 | 12/2011 | Riley et al. |
| 2011/0302719 A1 | 12/2011 | Schwirian et al. |
| 2011/0308019 A1 | 12/2011 | Terawaki |
| 2012/0026308 A1 | 2/2012 | Johnson et al. |
| 2012/0053424 A1 | 3/2012 | Kenalty et al. |
| 2012/0184862 A1 | 7/2012 | Foo |
| 2012/0253142 A1 | 10/2012 | Meger |
| 2012/0271122 A1 | 10/2012 | David et al. |
| 2012/0277637 A1 | 11/2012 | Vahdatpour |
| 2012/0323501 A1 | 12/2012 | Sarrafzadeh et al. |
| 2013/0091961 A1 | 4/2013 | Taylor |
| 2013/0249695 A1 | 9/2013 | Hann |
| 2013/0283530 A1 | 10/2013 | Main et al. |

(56) References Cited

U.S. PATENT DOCUMENTS

| | | |
|---|---|---|
| 2014/0157911 A1 | 6/2014 | Sarrafzadeh et al. |
| 2015/0045630 A1 | 2/2015 | Poliakine-Baruchi et al. |
| 2016/0228050 A1* | 8/2016 | Sugla .................. A61G 7/05776 |

FOREIGN PATENT DOCUMENTS

| | | |
|---|---|---|
| EP | 0264047 A2 | 4/1988 |
| EP | 0480471 A2 | 4/1992 |
| EP | 1211633 B1 | 6/2004 |
| EP | 2392304 A1 | 12/2011 |
| JP | H02078925 | 3/1990 |
| JP | 02232050 A | 9/1990 |
| JP | H6201502 A2 | 7/1994 |
| JP | H06281516 A | 10/1994 |
| JP | H07065943 | 7/1995 |
| JP | 10024073 A | 1/1998 |
| JP | 20020126007 A | 5/2002 |
| JP | 2004-245822 A | 9/2004 |
| JP | 2004-363759 A | 12/2004 |
| JP | 2005237684 A | 9/2005 |
| JP | 2006094903 | 4/2006 |
| JP | 2008027030 A | 2/2008 |
| JP | 2008-216016 A | 9/2008 |
| JP | 2010012335 A | 1/2010 |
| JP | 2010-043881 A | 2/2010 |
| WO | 2007106040 A1 | 9/2007 |
| WO | 20070106040 A1 | 9/2007 |
| WO | 2007121586 A1 | 11/2007 |
| WO | 2009048617 A2 | 4/2009 |
| WO | 2009065109 A1 | 5/2009 |
| WO | 2009138976 A2 | 11/2009 |
| WO | 2010092517 A1 | 8/2010 |
| WO | 2010102309 A1 | 9/2010 |
| WO | 2010119441 A2 | 10/2010 |
| WO | 2011091517 A1 | 8/2011 |
| WO | 2011111021 A2 | 9/2011 |
| WO | 2011113070 A1 | 9/2011 |
| WO | 2012056405 A2 | 5/2012 |
| WO | 2012114298 A2 | 8/2012 |
| WO | 2013008187 A1 | 1/2013 |
| WO | 2013021376 A1 | 2/2013 |
| WO | 2013105028 A2 | 7/2013 |
| WO | 2013156907 A2 | 10/2013 |
| WO | 2014024094 A2 | 2/2014 |
| WO | 2014064596 A2 | 5/2014 |

OTHER PUBLICATIONS

International Search Report and Written Opinion dated Feb. 6, 2018 for PCT/US17/59676 filed Nov. 2, 2017, 4 pages.

International Search Report and Written Opinion for PCT/IL2010/000294 dated Oct. 26, 2010.

International Search Report and Written Opinion for PCT/IB2011/051016 dated Oct. 9, 2012.

International Search Report and Written Opinion for PCT/IB2011/054773 dated Jun. 15, 2012.

International Search Report and Written Opinion for PCT/IB12/50829 dated Sep. 17, 2012.

International Search Report and Written Opinion for PCT/IB2012/053538 dated Dec. 17, 2012.

International Search Report and Written Opinion for PCT/IB13/52878 dated Oct. 29, 2013.

European Patent Office, Extended Search Report for the corresponding European Patent Application No. 12810788.5 dated Feb. 2, 2015.

International Search Report and Written Opinion for PCT/IB13/56287 dated Feb. 10, 2014.

International Searching Authority, The International Search Report and the Written Opinion for the corresponding international application No. PCT/IB13/59499 dated May 20, 2014.

International Search Report and Written Opinion for PCT/IB2013.050173 dated Jul. 1, 2013.

International Search Report and Written Opinion for PCT/IB2015/051822 dated Jul. 6, 2015.

Khan, Muhammad Ahsen, Dyeing of Wool and Silk Fibres with a Conductive Polyelectrolyte and Comparing Their Conductance, Report No. 2011.7.10, Masters in Textile Technology, University of Boras Sep. 2011, 53 pages.

Nouri, Mehdi, Conductivity of Textile Fibers Treated With Aniline, Iranian Polymer Journal, vol. 9, No. 1, 2000, 10 pages.

* cited by examiner

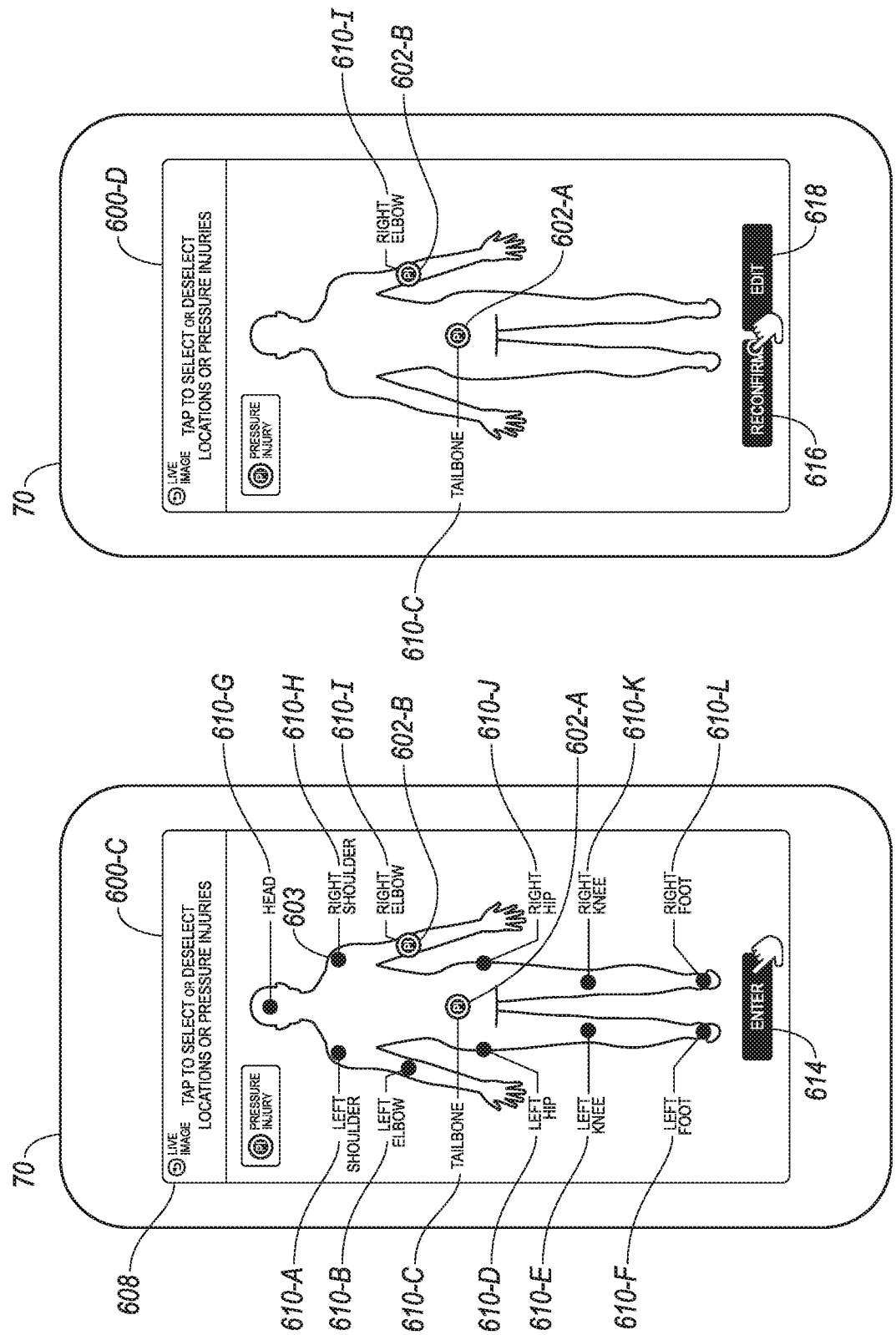

PATIENT VISUALIZATION SYSTEM

TECHNICAL FIELD

Aspects of the disclosure generally relate to a patient visualization system in connection with pressure injuries.

BACKGROUND

Pressure injuries, otherwise known as decubitus ulcers, pressure ulcers or bedsores, are lesions developed when a localized area of soft tissue of a subject is compressed between a bony prominence and an external surface for a prolonged period of time. Pressure injuries could appear in various areas of the body, such as elbows and knees. Development of pressure injuries based on a combination of factors, such as, unrelieved pressure, friction, shearing forces, humidity, and temperature.

Hospitalized patients often suffer from pressure injuries. However, pressure injuries are not limited to hospitalized patients. Individuals confined to wheelchairs are prone to suffer from pressure injuries, especially in their pelvis, lower back, and ankles. Although easily preventable or treatable if found early, if a pressure injury lingers, it becomes painful and treatment is both difficult and expensive. In many cases, pressure injuries can prove fatal, even under the auspices of medical care. According to one estimate, 2.5 million people suffer from pressure injuries in the United States each year, resulting in over 60,000 deaths annually.

An effective way of dealing with pressure injuries is to prevent their formation. A common preventive approach is maintaining a strict routine of repositioning, e.g., rotating and/or turning, a subject to offload, to eliminate, to alleviate and/or to reduce pressure every two (2) to three (3) hours. Research studies have shown that the effectiveness of caregiver repositioning techniques of patients is not adequate regardless of the level of experience and knowledge of the caregiver.

SUMMARY

In one embodiment, a system is disclosed. The system includes a processor, communicatively coupled to a pressure sensor device to periodically receive pressure sensor data experienced by a subject at locations on the pressure sensor device. The processor programmed to receive input indicative of an intervention resulting in a pressure lowering of a body area of the subject during a first high-pressure situation at a first time; and responsive to determining a second high-pressure situation at the body area of the subject at a second time later than the first time, display an indication of the input of the intervention in connection with the first high-pressure situation. Using the body position data and the associated pressure sensor data, the processor can calculate pressure experienced by one or more of the body areas of the subject over a period of time.

In another embodiment, a non-transitory computer-readable medium is disclosed. The non-transitory computer-readable medium has computer-readable instructions stored thereon that are configured to be executed by a processor to: receive input indicative of an intervention resulting in a pressure lowering of a body area of the subject during a first high-pressure situation at a first time; and responsive to determining a second high-pressure situation at the body area of the subject at a second time later than the first time, display an indication of the input of the intervention in connection with the first high-pressure situation.

In a third embodiment, a method is disclosed. The method includes receiving input indicative of an intervention resulting in a pressure lowering of a body area of the subject during a first high-pressure situation; and responsive to determining a second high-pressure situation at the body area of the subject at a second time later than the first time, displaying an indication of the input of the intervention in connection with the first high-pressure situation.

BRIEF DESCRIPTION OF THE DRAWINGS

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding. The description taken with the drawings makes apparent to those skilled in the art how the several selected embodiments may be put into practice. In the accompanying drawings:

FIGS. 6A-6D illustrate computer user interfaces of the system for identification of existing pressure injuries, adding new pressure injuries and removing such identifications;

DETAILED DESCRIPTION

Figure 1:
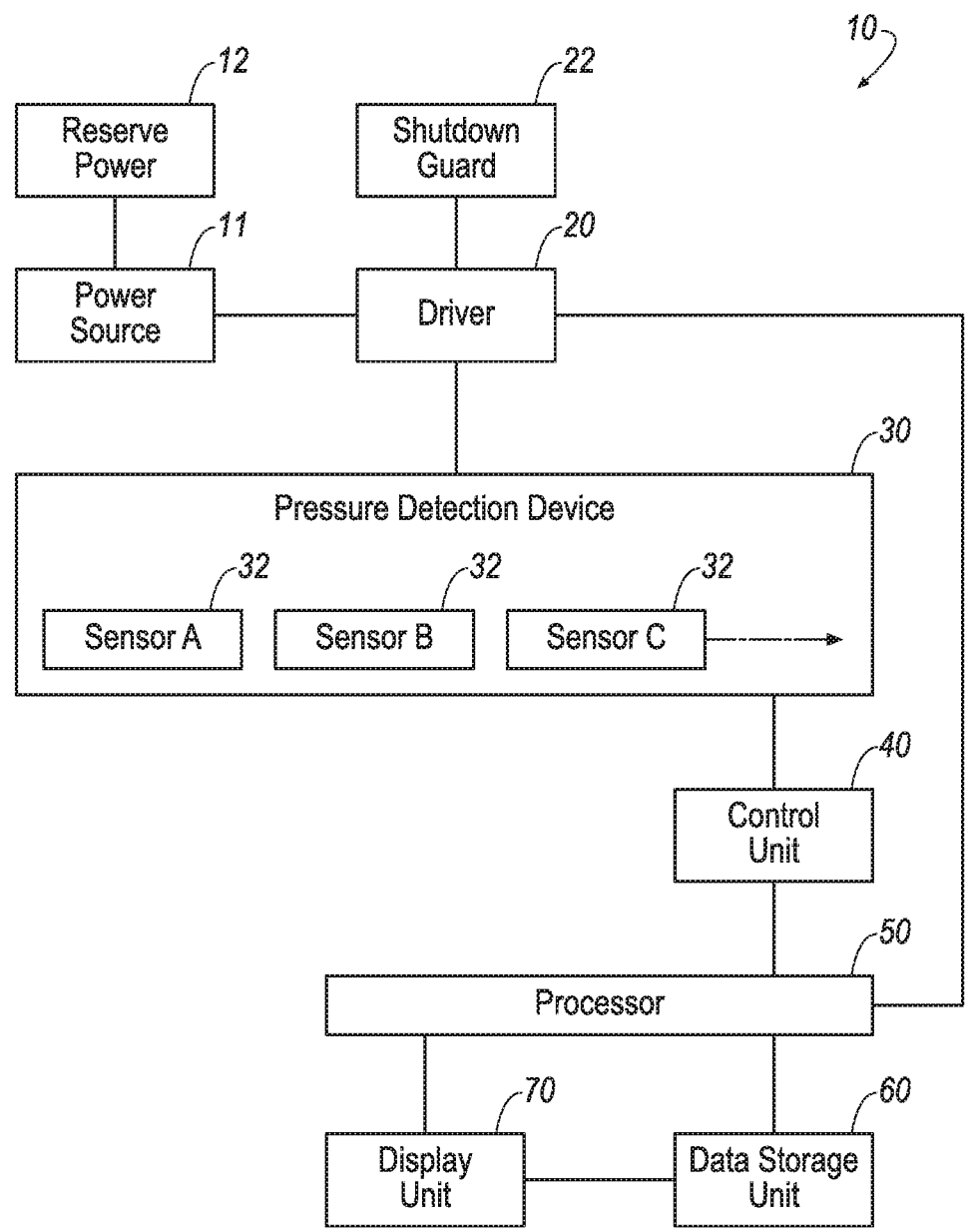
FIG. 1 is a schematic of the main components of a patient visualization system according to an embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Aspects of the disclosure generally relate to a patient visualization system in connection with pressure injuries. Research studies have shown that the effectiveness of caregiver repositioning techniques of patients is not adequate regardless of the level of experience and knowledge of the caregiver. Available computer pressure monitors are not sufficient because they do not provide computer user interfaces with the pressure history of patients from the operating room to the intensive care unit to the general population. What is needed is a patient visualization computer system that provides real-time, electronic delivery and display of actionable data that empowers medical staff to identify critical pressure injury situations, respond proactively and assist in the prevention of pressure injuries. The patient visualization computer system disclosed in embodiments of the present invention provides a technical solution to the technical drawbacks of currently proposed computer pressure monitors.

In embodiments of the present invention, the features of the patient visualization system may include real time monitoring and tracking of pressure injuries, tracking of body positioning and repositioning, tracking of pressure to those areas of the body that are susceptible to pressure injuries, tracking and measuring nurse/caregiver compliance, and providing nurses and patients with line of sight and actionable information that together allow nurses, primarily, but also, patients and their families/friends to make correct decisions and to take correct actions in effectively offloading patients. In certain embodiments, this includes computer user interfaces that show pressure experienced on specific body areas susceptible to pressure injuries over time. With this specific purpose software, the system allows clinicians to trend pressure exposure on specific body areas, and allows hospitals to trend pressure data to combat pressure injuries.

As one feature, the patient visualization system may detect and observe pressure experienced by a subject's body against a pressure detection mat or other detection surface. The system may provide a caregiver with a visual representation of the pressure experienced by the subject across the surface. The system may also provide a representation of pressure experienced by a body area over a designated period of time. Using the information regarding pressure to a body area over a period of time, a caregiver may take appropriate action, such as to reposition, e.g., rotate and/or turn, a subject to offload pressure to the body area.

To accurately measure pressure to a body area over a period of time, the system may be configured to associate pressure sensed by a pressure detection mat with a body area of a subject. For instance, the pressure detection mat senses pressure sensor data experienced by a subject over a period of time, the system determines the various levels of pressure over time based on the pressure sensor data and pixel pressure algorithm, the system determines body position over time based on the pressure sensor data over time and a body position algorithm, and the system associates the pressure over time and the body position over time to determine a pressure to a body area over a period of time. The body areas may be selected from a group of body areas susceptible to pressure injuries, e.g., head, left shoulder, right shoulder, left elbow, right elbow, tailbone, left hip, right hip, left knee, right knee, left foot, and right foot. In one embodiment, the system assigns a pressure for each of the body areas susceptible to pressure injuries even for such body areas that are not in contact with the pressure detection sheet. The associated sensor data may include sensor data indicative of an absence of pressure sensor data associated with one or more of the number of body areas, e.g., the body area is not in contact with the pressure sensor device during a period of time when the pressure sensor is collected, as opposed to other periods of time when the body area is in contact with the pressure sensor device.

A subject may change from a first body position to a second body position to a third body position. Within the first and third body positions, a body area may not be in contact with the pressure detection sheet, while the body area may be in contact with the pressure detection sheet. The system records a value indicative of an absence of pressure sensor data during the periods when the subject is in the first and third body positions and records a value indicative of the pressure sensor data while the subject is in the second body position. In one embodiment, these values are recorded continuously between changes in body position. By registering a value indicative of the lack of contact between the body area and the pressure detection sheet when a subject is not in bed or a certain body area is not experiencing pressure or very low levels of pressure is highly informative of offloading decisions.

The system may be further configured to provide a computer graphical representation of the various pressures to a body area over a period of time. As an example, for each tracked body area, e.g., a body area susceptible to pressure injury, the system displays a pie chart or other graph indicating the various levels of pressure to a body area over a period of time, e.g., over the last two (2) hours. The system may also be configured to display a peak pressure, signifying the value of the highest pressure pixel within a body area. Using these representations for the tracked body areas, a caregiver has useable information to determine body areas of concern for pressure injuries and to make educated decisions as to whether any of a subject's body areas susceptible to pressure injuries require offloading.

By using the results of the body position algorithm applied to the pressure sensor data, the system may be configured to display a body position history and reposition history over a certain period of time, e.g., the last three (3), six (6) or twelve (12) hours. The system can also be configured to display a representation within the body position history to identify and highlight when a reposition has not taken place during a required period of time, e.g., two (2) hours. Using this visualization, the caregiver has accurate information over time to determine when offloading should take place, or if it has not occurred. The system may also be configured to display a representation of body area pressure history that displays individual body area pressure history for a certain period of time, e.g. the last three (3), six (6) or twelve (12) hours. This representation provides pressure data over whatever the selected period of time is for each body area prone to pressure injuries.

When the system identifies a reduction in pressure on a tracked body area without a corresponding change in body position of the patient, the system may request information from the caregiver regarding what action, commonly referred to as "intervention," was performed to provide for the reduction in pressure. The system may provide a message including a listing of predefined choices from which the caregiver may select (e.g., lowered head of bed, raised head of bed, placed pillow/wedge under body area, removed foreign object, implemented a micro-shift of the top sheet, other, etc.). This action information may be retained by the system as part of the historical record for the subject, and may be viewable at a later date to allow caregivers to understand actions that were previously performed to the subject for offloading purposes.

The system may also use the recorded action information to provide predictive recommendations to the caregiver. In an example, responsive to the system identifying high pressure to a specific body area in a specific body position, the system may access subject historical data to locate similar conditions of body area and/or body position where the pressure was lowered by caregiver action. If a similar condition is identified, the system may present a message to the user indicating the intervention that was done to resolve the historical condition. Accordingly, the system may provide the caregiver with information regarding previous actions used to address high-pressure situations, without recommending any actions to be performed by the caregiver in the detected situation.

Reference is now made to the block diagram of FIG. 1, showing an embodiment of a patient visualization system 10. The system 10 may include at least one pressure detection device 30 including a plurality of sensors 32, a driver 20, a control unit 40 which may be connected to a power source 11, a processor 50, a data storage unit 60 and a display unit 70. Power may be supplied via a power cord connected to a wall outlet, or via battery power, optionally rechargeable. Battery support also allows for movement of the bed without requiring a powering off of the system 10. As a safety measure and for compliance tracking, caregiver authentication may be required via a shutdown guard 22 to confirm powering off of the control unit 40, such as with entry of a caregiver's employee identification number. While the system identified in FIG. 1 is a capacitive sensor system, in other embodiments, other methods can be utilized, such as resistive or piezoresistive systems.

The sensors 32 may be arranged at different locations on the pressure-detection device 30. In an example, the sensors 32 may be arranged in a two-dimensional grid across the surface of the pressure detection device 30. The driver 20 may supply voltage to the sensors 32 in the pressure detection device 30, and the processor 50 may measure the potential across the sensors 32, calculate impedance values for each sensor 32, and store the data in a data storage unit 60. The stored data may be further processed, analyzed, and displayed on the display unit 70, such as a computer screen, laptop, personal digital assistant (PDA), tablet device, mobile phone screen, printed sheet, or integrated display screen. Although presented in the block diagram of FIG. 1 as separate blocks, the system 10 may optionally be integrated into a stand-alone system.

Figure 2:
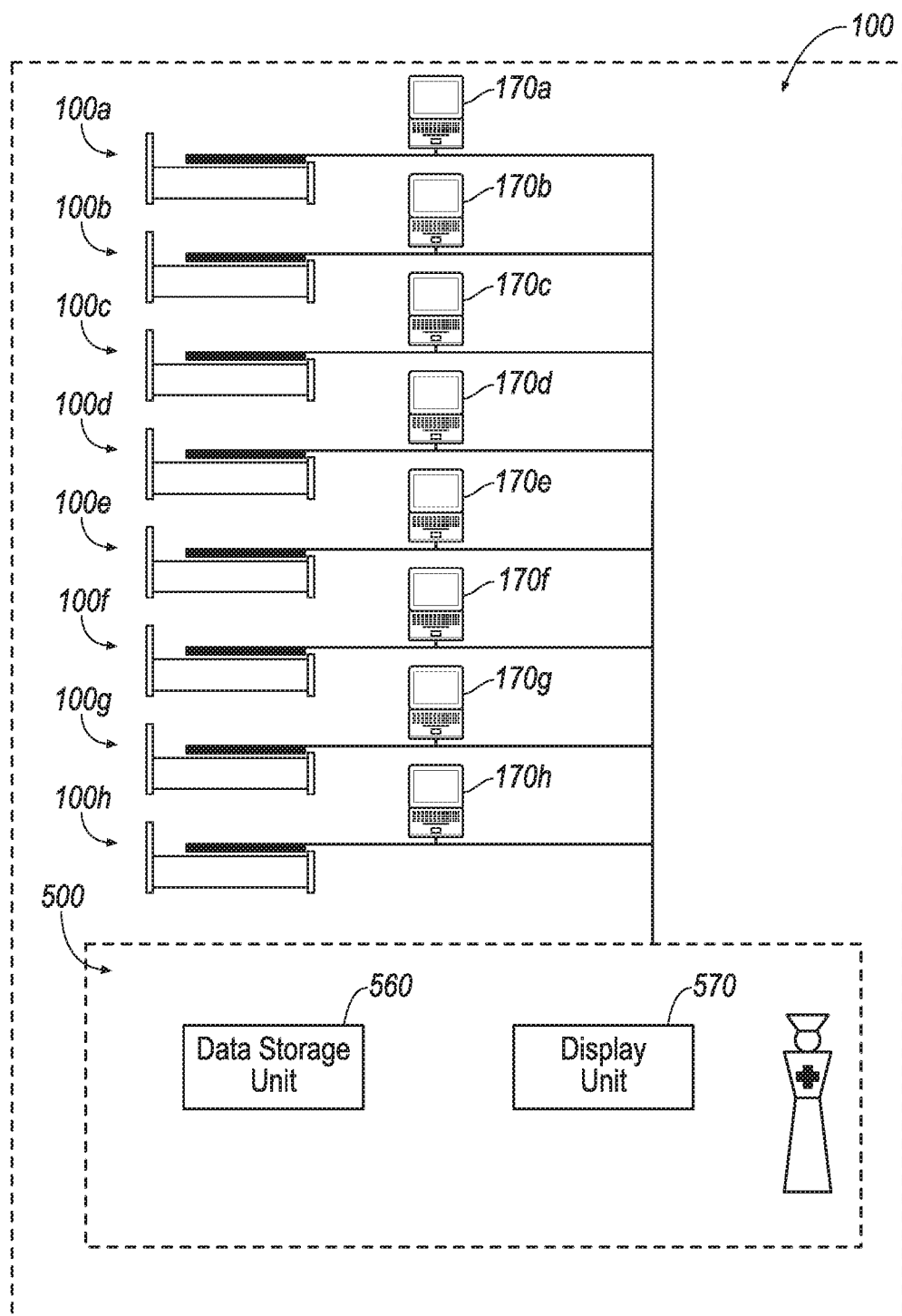
FIG. 2 is a schematic of an extended patient visualization system according to an embodiment.

Referring now to FIG. 2, an extended patient visualization system 100 may include a number of sub-systems 100a-100h in communication with a common remote control center 500. The sub-systems 100a-100h may be, for example, beds in a hospital or care home, and may be configured to communicate with the common remote control center 500, for example at a nursing station. This communication can be provided via wiring to a nurse call system, or alternatively via wireless communication (e.g., BLUETOOTH, ZIGBEE, Wi-Fi, cellular, etc.) to the nursing station. Alternatively, the plurality of sub-systems 100a-100h may be located remotely from one another, for example each in an individual home, and the remote control center 500 may be a manned observation station.

The remote control center 500 may include a data storage unit 560 for storing data from the sub-systems 100a-100h and a display unit 570 for presenting and/or displaying the data as required. The remote control center 500 may additionally provide processing and driving functionality for controlling multiple sub-systems. Optionally, each sub-system 100a-100h may have its own dedicated display unit 170a-h for processing, storing and displaying data locally.

Figure 3A:
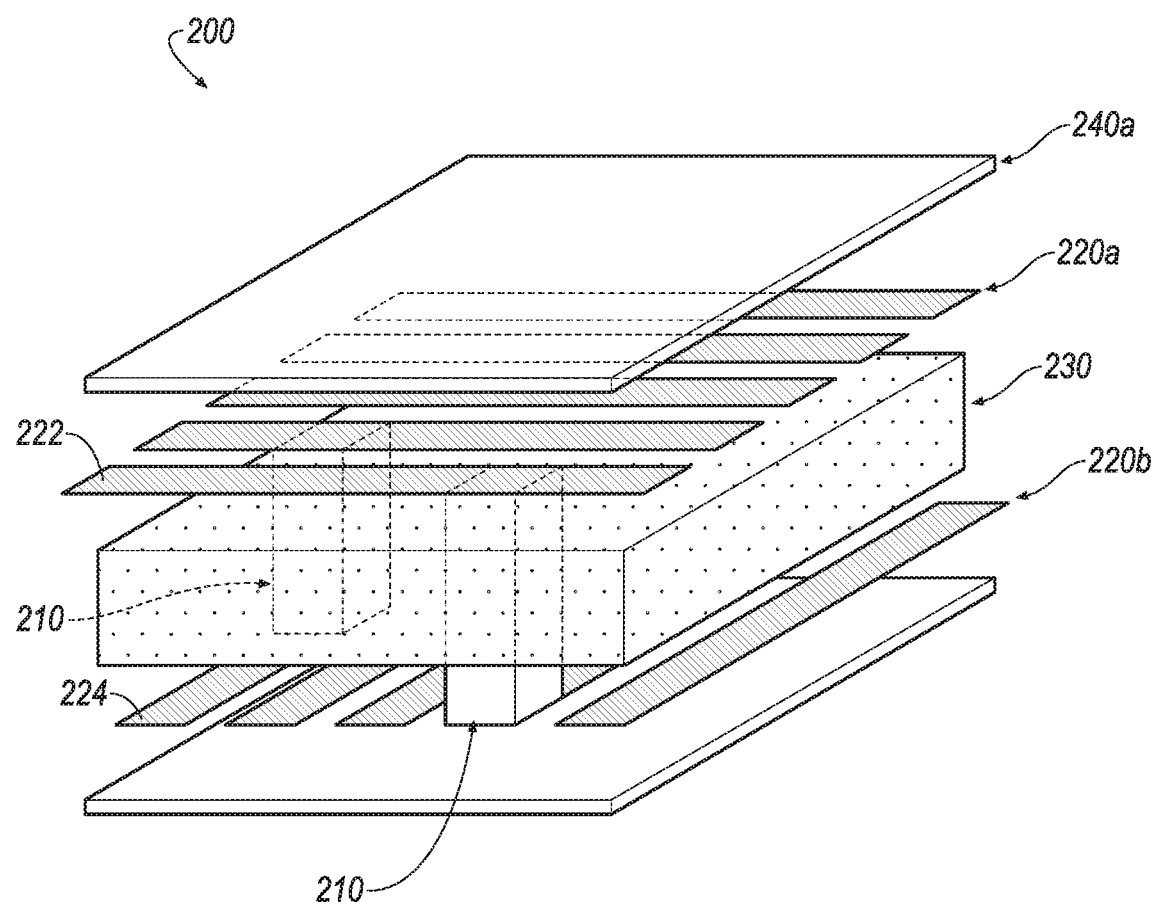
FIGS. 3A-3D depict exploded, perspective views of multiple embodiments of pressure detection devices.

Reference is now made to FIG. 3A showing an embodiment of a pressure detection device 30 as a pressure detection sheet or mat 200. The pressure detection sheet 200 includes capacitive sensors 210 arranged in a form of a matrix. The sheet 200 may have two layers 220a, 220b of conductive material separated by an insulating layer 230 of isolating material. Each of the conductive layers 220a, 220b may include parallel conductive strips 222, 224 and the two conductive layers 220a, 220b of strips 222, 224 may be arranged orthogonally such that in one conductive layer 220a the strips 222 are horizontal and in the other conductive layer 220b the strips 224 are vertical. Horizontal and vertical are used herein to describe the relative relationship of strips 222, 224 to one another, and these terms are not intended to be limiting. Each strip 222, 224 may be wired to a control unit and may operate under a low voltage source.

The sensors 210 incorporated in the pressure detection sheet 200 may provide measurements based on the capacitance between the sections of the conducting strips 222, 224 overlapping at each "intersection" of a vertical conductive strip with a horizontal conductive strip. These capacitive sensors 210 may be configured such that pressure on the surface of the pressure detection sheet 200 changes the spacing between the two conductive layers 220a and 220b, and consequently changes the capacitance of the intersections of the strips 222, 224.

The driver 20 may provide an oscillating electric potential across each sensor 210 and may measure the alternating current produced. For instance, the driver 20 may provide an electric potential to one of the strips (e.g., strip 222) and may measure the electrical potential on the other strip (e.g., strip 224), such that the capacitance of the overlapping section (i.e., capacitive sensors 210) may be determined. Thus, the driver 20 may calculate the impedance of the intersection of the strips 222, 224 and determine the capacitance of the intersection from the impedance. Accordingly, where the mechanical properties of the sensors 210 are known, the driver 20 may deduce the pressure on the sensors 210 of the pressure detection sheet 200.

To make a stable reading of impedance values from a row of sensors 32, little or no movement should be made by the subject during the taking of readings from the sensors 32. Accordingly, in certain embodiments, the time taken for readings may be of the order of tens or hundreds of milliseconds, during which movement of the subject is generally insignificant. In applications where the subject is largely immobile, longer reading times may be used.

In some embodiments, the materials for the conductive layers 220a, 220b and insulating layers 230 are flexible. The insulation material may be a compressible sponge-like, airy or porous material (e.g., foam), allowing for a change in density when pressure is applied to it.

The pressure detection sheet 200 may be placed underneath or otherwise integrated with other material layers 240a, 240b such as used in standard bed sheets. The additional materials may confer further properties as needed for a particular application. The conductive material of the sensors 210 may be wrapped by an isolating, water resistant, breathable cover sheet or the like, allowing minimum discomfort to the subject resting on the sheet.

Figure 3B:
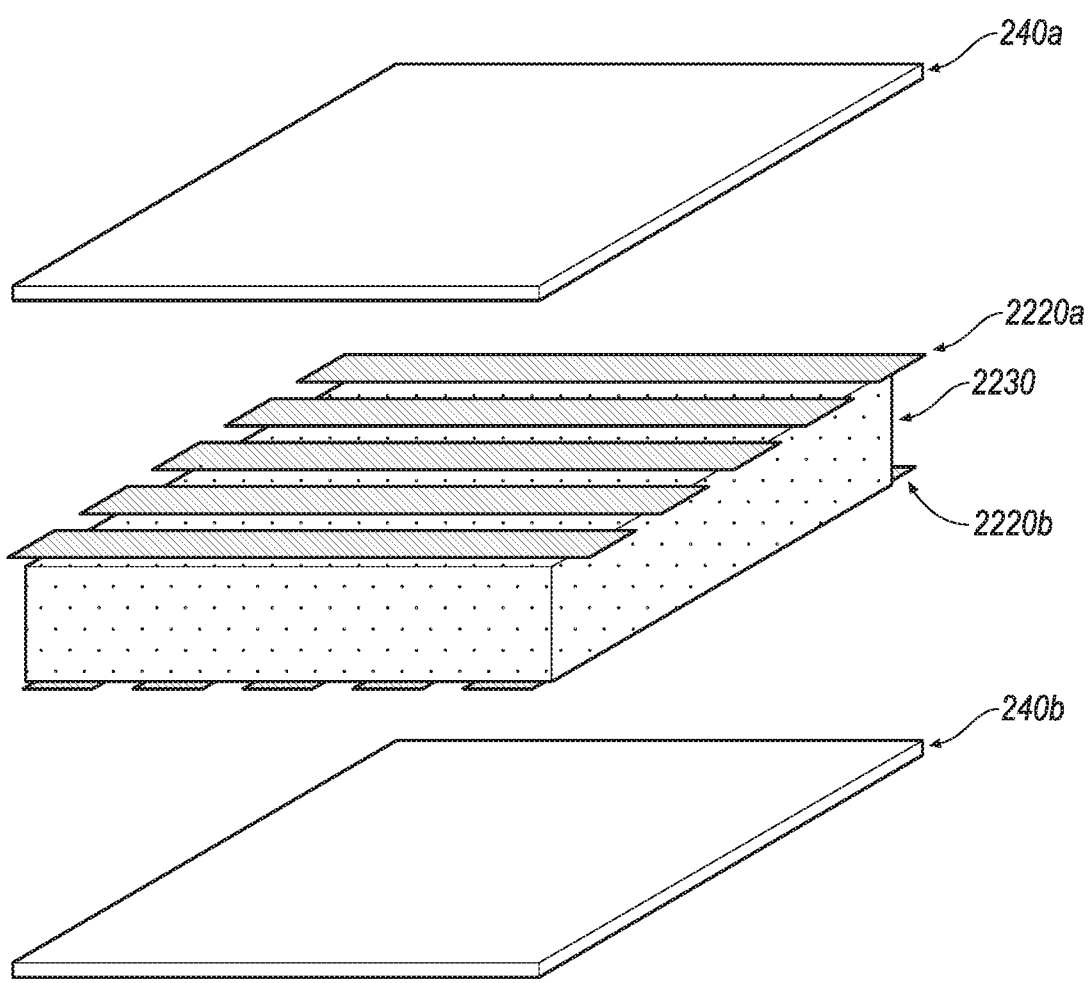
Figure 3C:
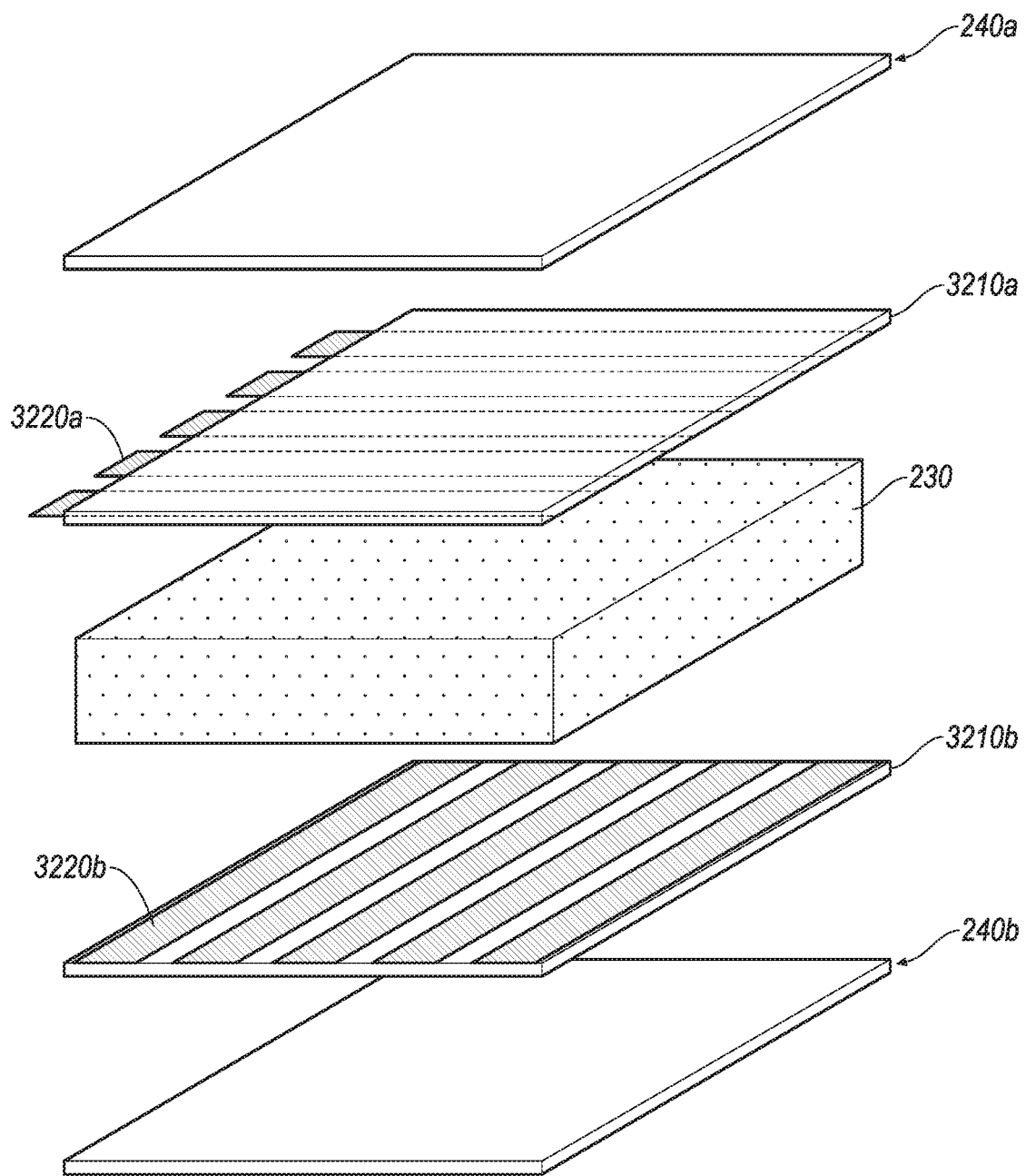
Figure 3D:
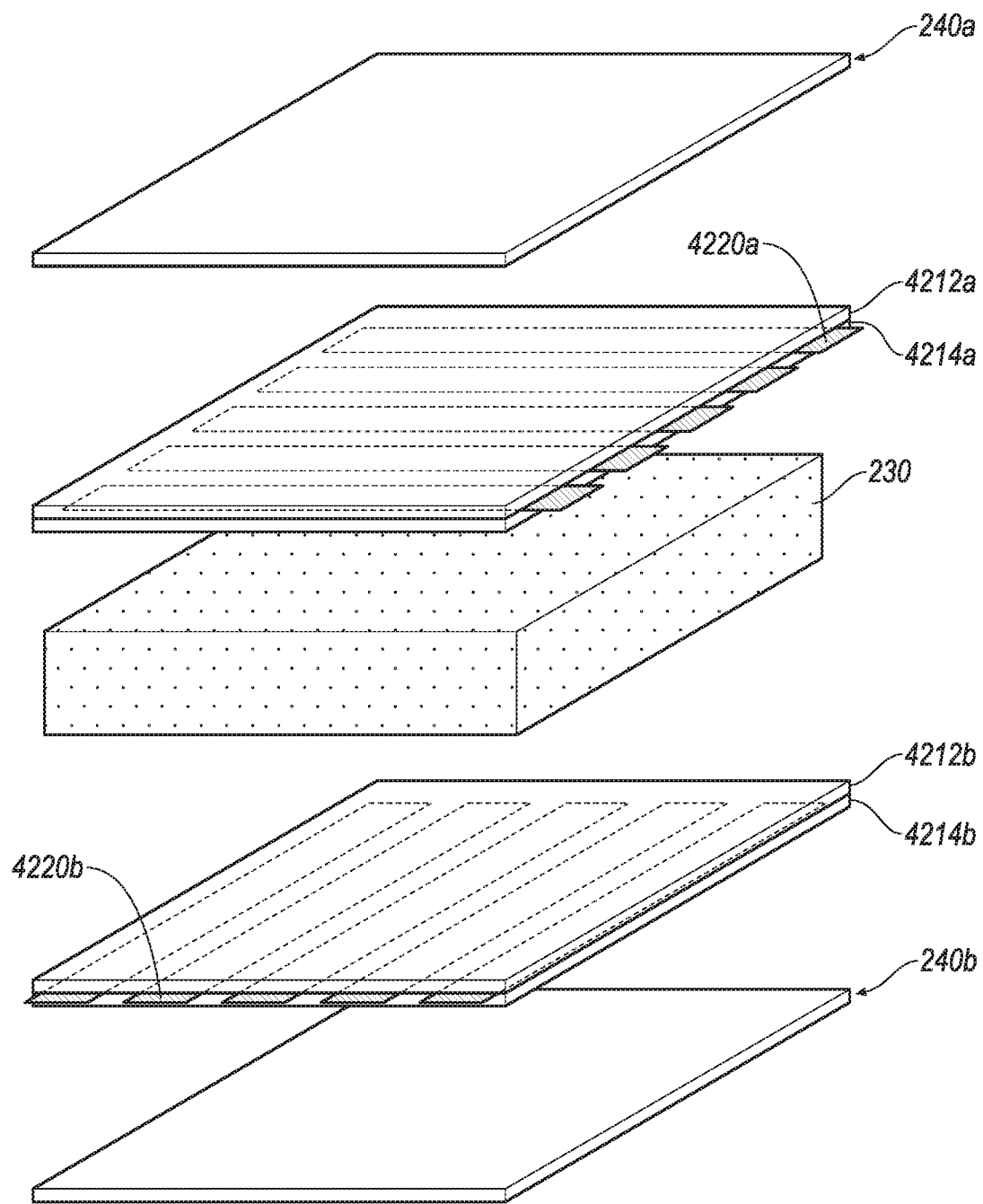

With reference now to FIGS. 3B-3D showing sections of other embodiments of the pressure detection sheet 200, the conductive layers 220 (FIG. 3A) may be supported by various substrates. For example, FIG. 3B shows two conductive layers 2220a, 2220b adhered or otherwise attached to the insulating layer 2230. Alternatively, as shown in FIG. 2C, conductive layers 3220a, 3220b may be supported by separate substrates 3210a, 3210b, for example thermoplastic polyurethane, the insulating layer 230 being sandwiched therebetween. In still another embodiment, as shown in FIG. 2D, the conductive layers 4220a, 4220b may themselves each be sandwiched between two substrates 4212a, 4214a, 4212b, 4214b, respectively.

Figure 4A:
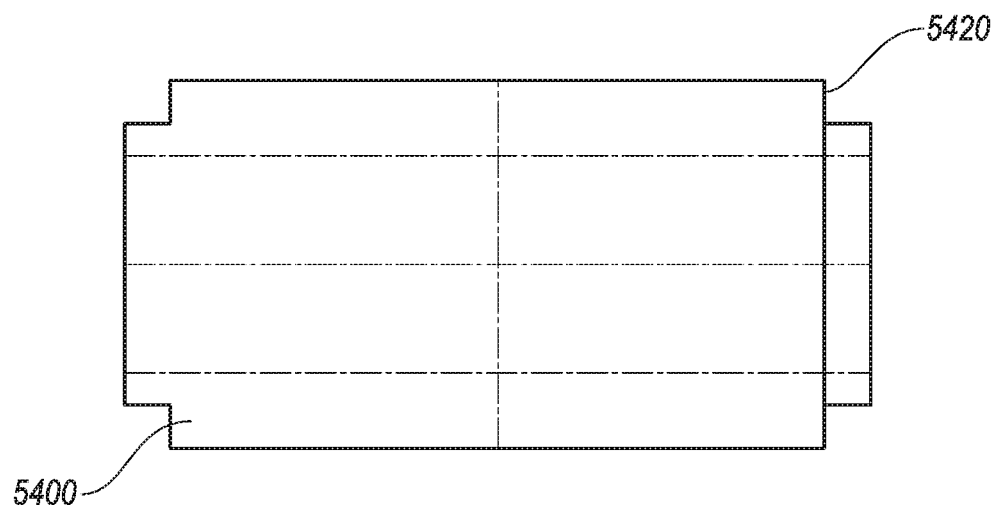
FIGS. 4A and 4B depict a top plan view and a fragmented view, respectively, of another embodiment of a pressure detection sheet.
Figure 4B:
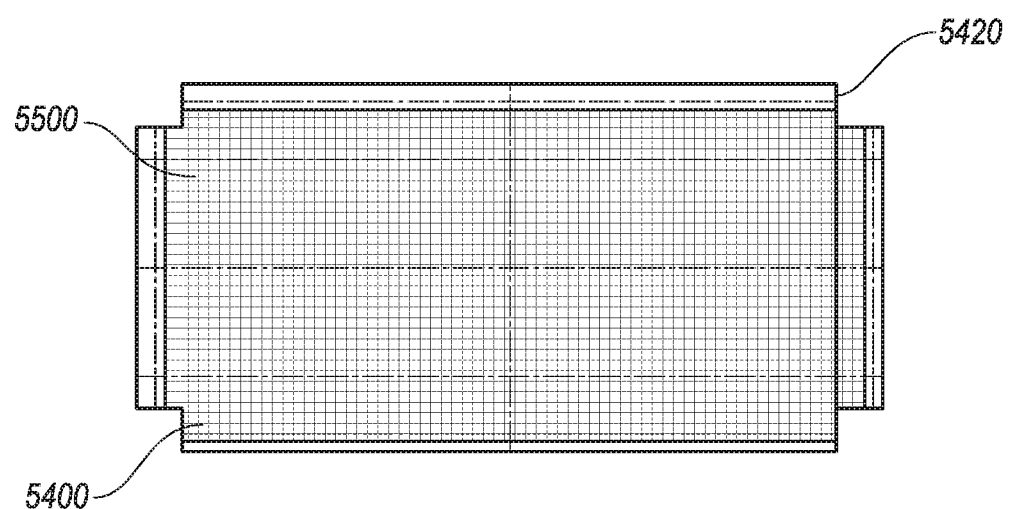

With reference to FIGS. 4A and 4B, a top view and a fragmented view, respectively, are shown of a further embodiment of a pressure detection sheet 5000. The pressure detection sheet 5000 includes a sensor matrix 5500, such as described above, housed within a cover sheet 5400 and which may be sealed by a zipper 5420, or other fastener, as required.

Figure 5:
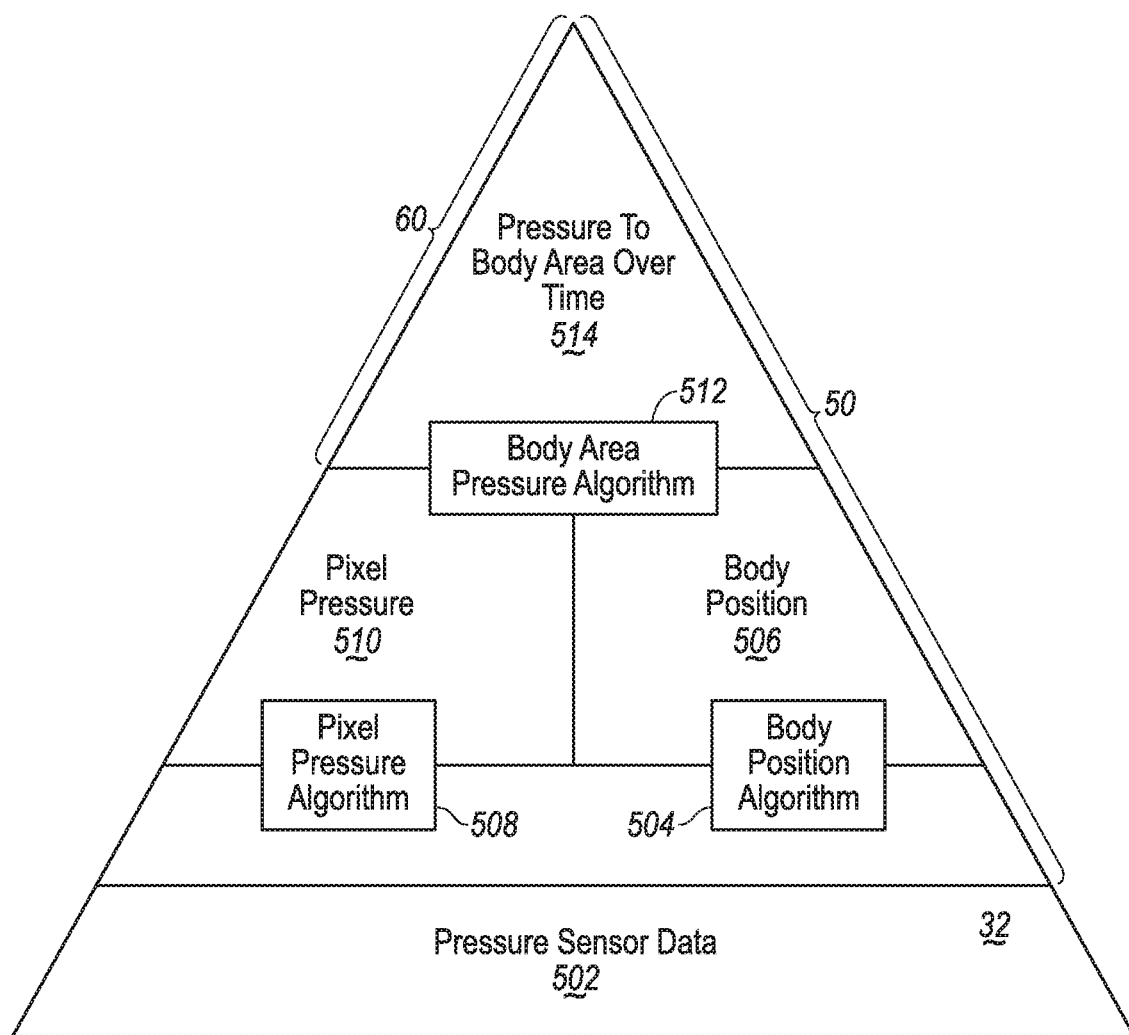
FIG. 5 is a data flow diagram of the processing of sensor pressure data performed by the processor of a patient visualization system.

With reference to FIG. 5, the processor 50 may receive pressure sensor data 502 from the sensors 32 of the pressure detection device 30, and utilize a body position algorithm 504 to determine a body position 506 of the subject based on a position library. The processor 50 may further use a pixel pressure algorithm 508 to determine pixel pressure 510 exerted on the pressure detection device 30 based on the pressure sensor data 502. The body position 506 and the pixel pressure 510 are used by body area pressure algorithm 512 to determine pressure to a body area over a period of time 514.

The processor 50 may be implemented as a combination of hardware and software, and may include one or more software applications, modules, or processes stored in memory for causing one or more computing devices to perform the operations described herein. The body position algorithm 504, pixel pressure algorithm 508, body area pressure algorithm 512, and other operations and algorithms described with respect to the data flow of FIG. 5 may be such applications, modules, or processes, and may be implemented at least in part by instructions stored on one or more non-transitory computer-readable media. In one or more embodiments, a "pixel" may represent a single sensor of the sensors 32.

The pressure sensor data 502 may include data indicative of the pressure exerted on each of the sensors 32 of the pressure detection device 30. In an example, the pressure sensor data 502 may include a pressure distribution image or data set having a set of readings taken from each of the sensors 32 of the pressure detection device 30. In another example, the processor 50 may form the pressure sensor data 502 into a pressure distribution histogram (sometimes referred to as a pressure distribution signature vector) by creating a one-dimensional array, or vector, of the pressure sensor data 502 relating to a pressure image feature.

Various approaches may be used by the processor 50 to generate pressure distribution signature vectors from pressure distribution images. As an example, a signature vector of a maximum point distance feature may be obtained by: removing pixels having pressure values below a first threshold; identifying local maxima by selecting pixels whose pressure values are greater than or equal to all bordering pixels; clustering the local maxima into sets of a given size; obtaining a point average for each set of maxima, perhaps by calculating a spatial average therefor. Accordingly, an output vector may be generated arraying the distances between the local maxima average points. Another approach may be used for generating a pressure distribution signature vector including a histogram of pressure values. Optionally, the pressure value of each pixel may be arrayed into a histogram of total pressure values. Alternatively, or additionally, a partial pressure histogram may be generated by: calculating a spatial average for all values below a threshold value, the values being weighted for their positions; calculating the spatial averages; choosing a square of twice the standard deviation of data relative to the average position point; calculating a histogram of values out of this square. Still another approach may be used for generating a pressure distribution signature vector based upon the position of the pixels. The values of pixels may be selected where the pixel location is within a defined range.

The body position 506 may be an indication of the body position of a subject recumbent on the pressure detection device 30. In an example, the body position 506 may include a back-side resting body position, a right side resting body position, a stomach or front-side resting body position, an out of bed position, or a left side resting body position. In one or more embodiments, the body position 506 may further indicate one or more position variants of the identified body position. For instance, the body position 506 may indicate an amount of lean of the subject to the right or to the left, an amount of shift or angle of one or more limbs of the subject, and/or an amount of turn of the head of the subject.

The position library may include a set of reference pressure images corresponding to various body positions. Each image of the position library may include data representative of a model of a body position and an association of the data with an identifier of the body position represented by the data. The data of the reference pressure images may include a pressure distribution image and/or a pressure distribution histogram. To create the position library, an operator may record samples of subjects adopting known body positions and may store the pressure images or their associated pressure histograms in the position library.

The body position algorithm 504 may utilize the pressure sensor data 502 and the position library to identify the body position 506 of the subject. The identification may enable body features (e.g., body areas) to be recognized as well as for the pressure sensor data 502 to be associated with a body coordinate system. In an example, the body position algorithm 504 may compare the pressure sensor data 502 to the reference position images of the position library, and may determine which of the reference position images of the position library best matches the pressure sensor data 502.

The body position algorithm 504 may further identify a period of time during which the subject is in each recorded position.

The body position algorithm 504 may implement one or more of various comparison algorithms to compare the recorded pressure image of the pressure sensor data 502 to the candidate images of the position library. These comparison algorithms may include, for example, particle component analysis, support vector machine, K-mean, two-dimensional fast Fourier analysis, earth movers distance, and the like.

As a more specific example, the body position algorithm 504 may compare the recorded pressure image of the pressure sensor data 502 and the candidate images of the position library by comparing pressure distribution histograms of the recorded image and the candidate image. The histogram may serve as a signature of the pressure image features, and the body position algorithm 504 may utilize a comparison method to provide a similarity rating between feature signatures.

The pixel pressure algorithm 508 may be configured to determine pixel pressure 510 exerted on the pressure detection device based on the pressure sensor data 502. In an example, the pixel pressure algorithm 508 may assign pressure values from the pressure sensor data 502.

The body area pressure algorithm 512 determines pressure to a body area over a period of time based on pixel pressure 510, body position 506 and body areas. The body area pressure algorithm 512 may assign body areas in which there is an absence of pressure sensor data a pressure value indicative of this absence.

The result of the process and algorithms set forth in FIG. 5 may be referred to as pressure to a body area over a period of time 514, and may be stored in the data storage unit 60 or other data store of the system 10. In an example, the pressure to a body area over a period of time 514 may include for each timeframe, an indication of the body position 506 of the subject, as well as the pressure values corresponding to the body areas, whether or not the body areas were in contact with the pressure detection device 30 or otherwise exerting pressure. Accordingly, the pressure to a body area over a period of time 514 may include body pressure values for body areas being tracked based on the body area selection, even when there is an absence of pressure sensor data associated with one or more of the number of body areas, e.g., the body area is not in contact with the pressure sensor device during a period of time when the pressure sensor data is being collected, as opposed to other periods of time when the body area is in contact with the pressure sensor device.

The body areas may include a listing of body areas that are susceptible to pressure injuries. These body areas may include bony prominences, which are areas in which bones are close to the surface of the body. In an example, the body areas may include the head, shoulders, hips, knees, feet, tailbone, elbows, heels, and spine. The body areas selection may include identification of the predefined body areas that are selected by a caregiver, e.g., body areas that have a pressure injury currently or in the recent past.

FIGS. 6A-6D illustrate user interfaces 600 of the system for identification of existing pressure injuries, adding new pressure injuries, and removing such identifications. In one or more embodiments, the user interfaces 600 are configured to receive touch screen input. In an example, the user interfaces 600 may be presented to the caregiver via the display unit 70. The user interfaces 600 may be presented responsive to the caregiver requesting to adjust the body areas to be observed, or responsive to the system 10 otherwise wishing to confirm the body areas, such as when a subject lies down on the pressure detection device 30 after not lying on the pressure detection device 30.

In one embodiment, a pressure signature algorithm can record a pressure signature of a subject to determine whether or not the same patient is lying on the device 30 after not lying on the device 30. The pressure signature algorithm can determine from the current pressure signature and a historic pressure signature whether the same patient is lying on the pressure detection device 30 within a margin of error, e.g., 5.0%, 1.0%, 0.1% to 0.01%. If the determination is within the margin of error, then the system 10 assumes that the same subject is present. If the determination is outside of the margin of error, the system uses its defaults settings, e.g., if there is no patient lying on the device 30 for more than a time threshold, e.g., 2 hours, then the system defaults to a new person is lying on the device 30, and if it is less than the time threshold, e.g., 2 hours, then the system defaults to the same person lying on device 30.

Figure 6B:
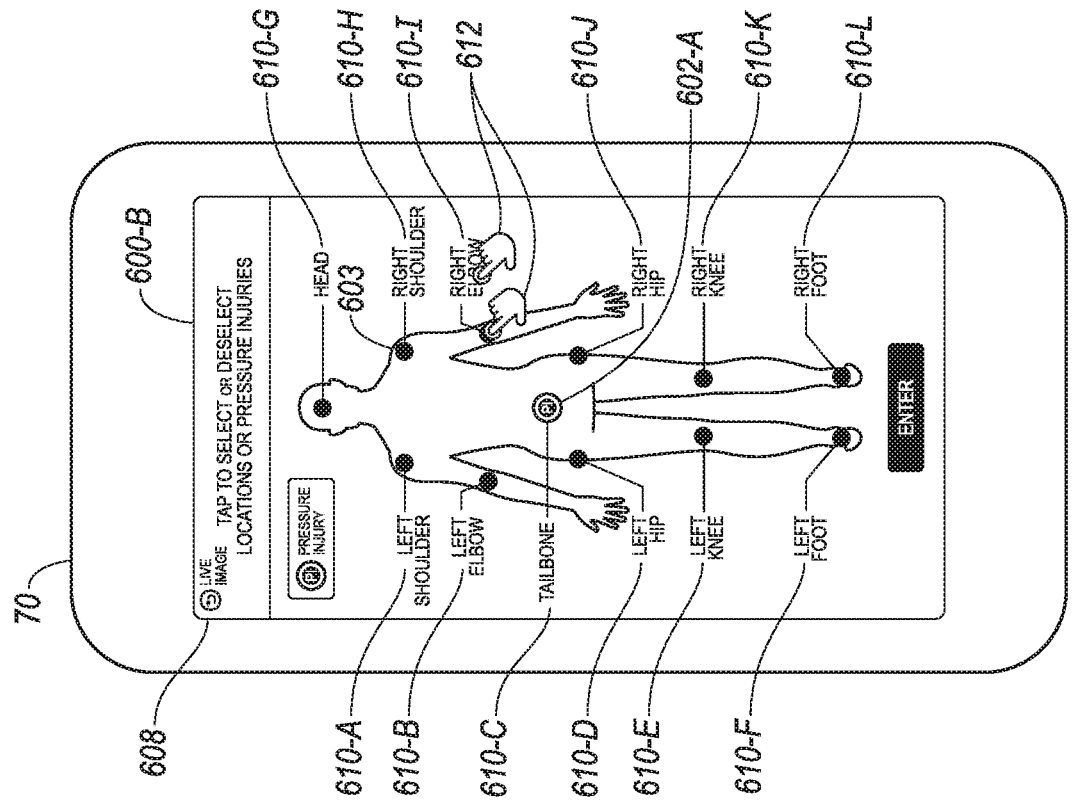
Figure 6A:
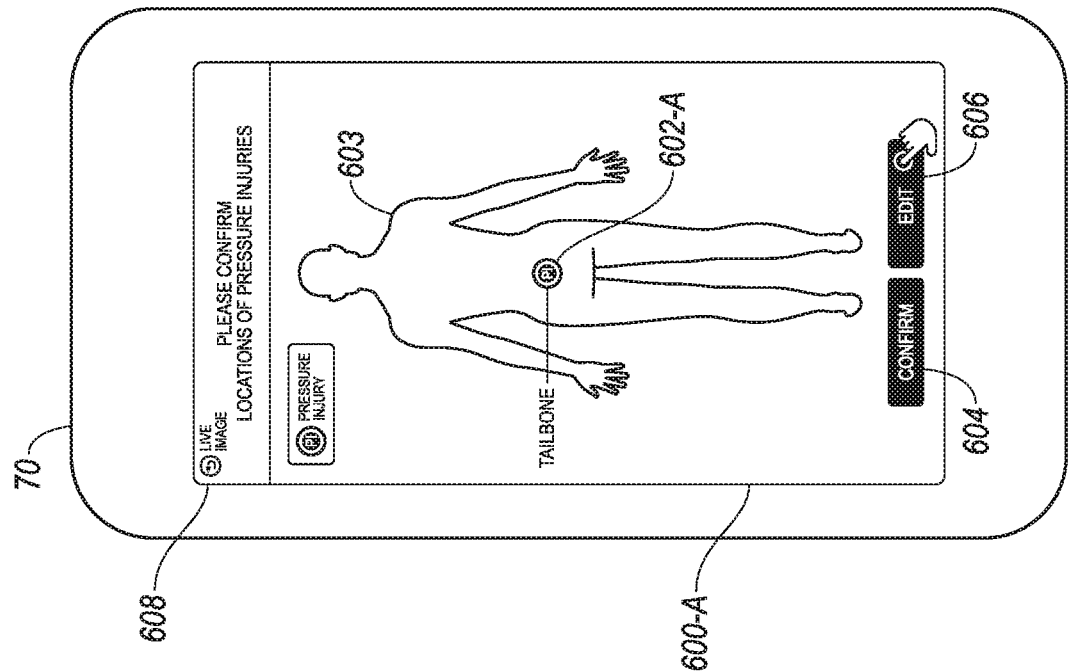

FIG. 6A depicts a user interface 600-A to display one or more body areas currently selected to indicate the presence of a pressure injury in the one or more body areas of the subject. Pressure injury icon 602-A can be shown at each of the one or more body areas selected relative to a representation 603 of the subject. The representation 603 as shown in FIG. 6A is a back-side resting body position representation of the subject. A front-side resting body position representation is also contemplated by one or more embodiments. As shown in FIG. 6A, a pressure injury icon 602-A is shown at the tailbone body area of the subject as depicted by representation 603. User interface 600-A includes a confirm control 604 and an edit control 606. When selected, the confirm control 604 confirms the selected one or more body areas as having a pressure injury. When selected, the edit control 606 permits the user to select additional body areas having pressure injuries and to deselect body areas in which a pressure injury is no longer present. User interface 600-A also includes a live image control 608. Upon selection of the live image control 608, the display unit 70 displays a live image of the subject, such as, the user interface 700 depicted in FIG. 7 and described below.

Upon selection of the edit control 606, user interface 600-B of FIG. 6B may be displayed. FIG. 6B includes a number of body area controls 610 that relate to a corresponding body area and are configured to allow for selection and deselection of the corresponding body area. For instance, in the illustrated example, the body area controls 610 include a left shoulder body area control 610-A, a left elbow body area control 610-B, a tailbone body area control 610-C, a left hip body area control 610-D, a left knee body area control 610-E, a left foot body area control 610-F, a head body area control 610-G, a right shoulder body area control 610-H, a right elbow body area control 610-I, a right hip body area control 610-J, a right knee body area control 610-K, and a right foot body area control 610-L.

As shown in the user interface 600-B, the tailbone body area control 610-C has been selected. As depicted by a selector icon 612, a user is in the process of selecting right elbow body area control 610-I. Once selected, a pressure injury icon 602-B is displayed on the right elbow body area of representation 603 as shown in FIG. 6C. As further shown in FIG. 6C, the selector icon 612 is used to select the enter control 614 to enter the selection of the right elbow body area control 610-I into the data storage unit 60 of system 10.

The user interface 600-D of FIG. 6D includes indications of which selectable body area controls 610 are currently selected for the subject. For instance, in the illustrated example the tailbone body area control 610-C and the right elbow body area control 610-I are selected. If the caregiver is satisfied with these selections, the caregiver may select the reconfirm control 616 to confirm the body area selections. If not, the caregiver may select the edit control 618 to allow the caregiver to edit the body area selection.

Representation 603 of FIGS. 6A-6D is a back-side resting body position representation of a subject. Similarly, a user interface may include a front-side resting body position representation of a subject, over which body area controls 610 may be positioned. The front-side resting body position user interface may also include a representation of which resting side of the subject is being represented. Moreover, the body area controls 610 may correspond to body areas visible from the front-side resting body position of the subject rather than the back-side resting body position of the subject.

Figure 7A:
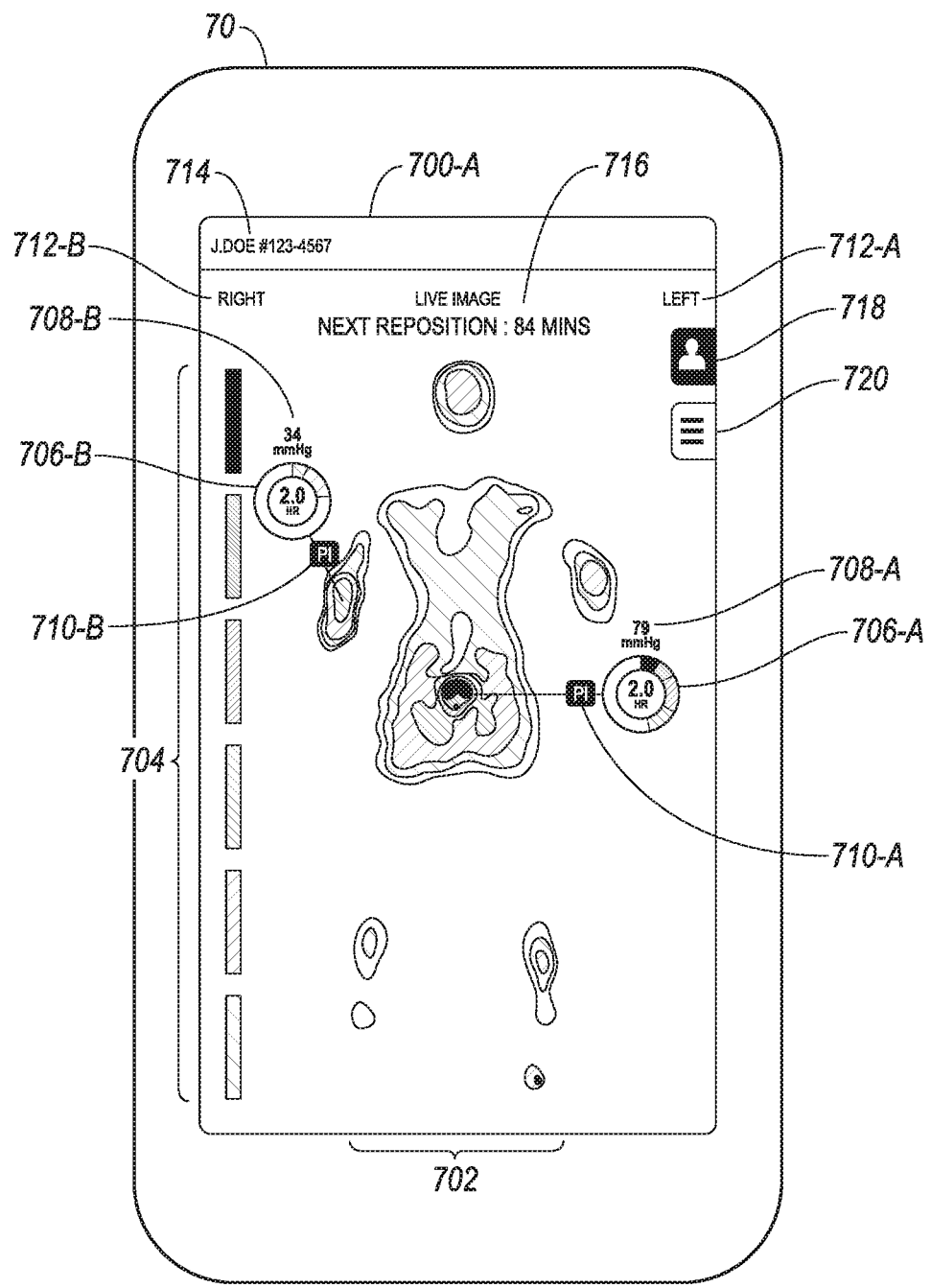
FIGS. 7A and 7B illustrate computer user interfaces of the system for display of live and historical pressure assessment and observation of a subject.

FIG. 7A illustrates a user interface 700-A of the system 10 for display of live and historical pressure assessment and observation of a subject. The user interface 700-A may be presented to the caregiver via the display unit 70.

The user interface 700-A may include a body area pressure representation 702 indicating current subject body area pressure values based on the pressure sensor data 502, to allow the caregiver to understand which areas are of greater or lesser pressure as part of a live pressure assessment. The body area pressure representation 702 may distinguish areas of different pressure according to various visual mechanisms. For instance, areas of higher pressure are displayed in different colors or patterns as compared to areas of lower pressure. The values of the body area pressure representation 702 may be specified along a scale illustrated by a legend 704. In an example, the legend 704 may specify values or ranges of high pressure in red, and values of decreasing pressure as colors along a red-orange-yellow-green-blue color spectrum, for example. In one embodiment, a red range is 75+ mmHg, an orange range is 60-74 mmHg, a yellow range is 45-59 mmHg, a green range is 30-44 mmHg, a light blue range is 15-29 mmHg, a blue range is 1-14 mmHg and a black value is 0 mmHg.

The user interface 700-A includes body area pressure history indications 706 associated with the pressure representation 702 of the subject. FIG. 8 shows a magnified view of a body area pressure history indication 706. The body area pressure history indications 706 may be configured to provide graphical representations of the pressure against each body area selected. The user interface 700-A depicts body area pressure history indications 706-A and 706-B for the right elbow body area and the tailbone body area, respectively. These body areas were selected as body areas with existing pressure injuries as depicted in FIGS. 6A-6D. As shown in FIG. 7-A, the pressure representation is a front-side resting body position representation of the subject; although a back-side resting body position representation is also contemplated.

For each tracked body area, e.g., the right elbow body area and the tailbone body area as shown in FIG. 7A, the user interface 700-A displays a body area pressure history indication 706. The body area pressure history indication 706 is a graphical representation configured to visualize the pressure to a selected body area over a period of time, e.g., the interval of the reposition timer. As shown in FIG. 7A, the body area pressure history indication is a pie chart. As shown, the pie chart displays the amount of time within each different pressure category, level or range, including no pressure, using the same color coding as the body area pressure representation 702. These amounts of time within each different pressure category, level or range are shown for the time period designated by the number in the center of the pie chart, e.g., the interval of the reposition timer, which can be adjusted by the caregiver within system 10. In one embodiment, the default for the reposition interval is two (2) hours. These amounts of time are displayed starting at a twelve o'clock position on the pie chart and represent each amount of time within each pressure category, level or range from high to low in a clockwise orientation. The user interface also includes an indication of peak pressure 708, signifying the highest pressure registered at any pixel within the body area at that moment or instant of time. FIG. 8 shows an exploded view of an indication of peak pressure 708.

As shown in the user interface 700-A, each body area pressure history indication 706 may include a mark surrounding the corresponding tracked body area to which the graphical representations of the pressure over time is linked, e.g., by a lead line.

The user interface 700-A includes pressure injury indications 710 for those body areas previously identified by the caregiver during setup as currently having pressure injuries. For instance, the body area pressure history indications 710-A and 710-B are indicated as currently having a pressure injury. In one embodiment, those body area pressure indications associated with a current pressure injury are always displayed on user interface 700-A.

The user interface 700-A may also include side indications 712 to aid the caregiver in understanding the positioning of the subject. As shown in FIG. 7A, left side indication 712-A is on the right side of user interface 700-A and right side indication 712-B is on the left side of user interface 700-A. Accordingly, the left side of the subject is depicted on the right side of the user interface 700-A and the right side of the subject is depicted on the left side of the user interface 700-A.

The user interface 700 may also include a subject identifier 714 to indicate to the caregiver the name and/or identifier of the subject. The user interface 700 may also include further controls, such as a reposition timer 716 indicating when the subject should next be repositioned. It should be noted that the user interface 700 are merely examples, and more, fewer, or different layouts of controls including body area pressure history indications 706 may be used.

Figure 9:
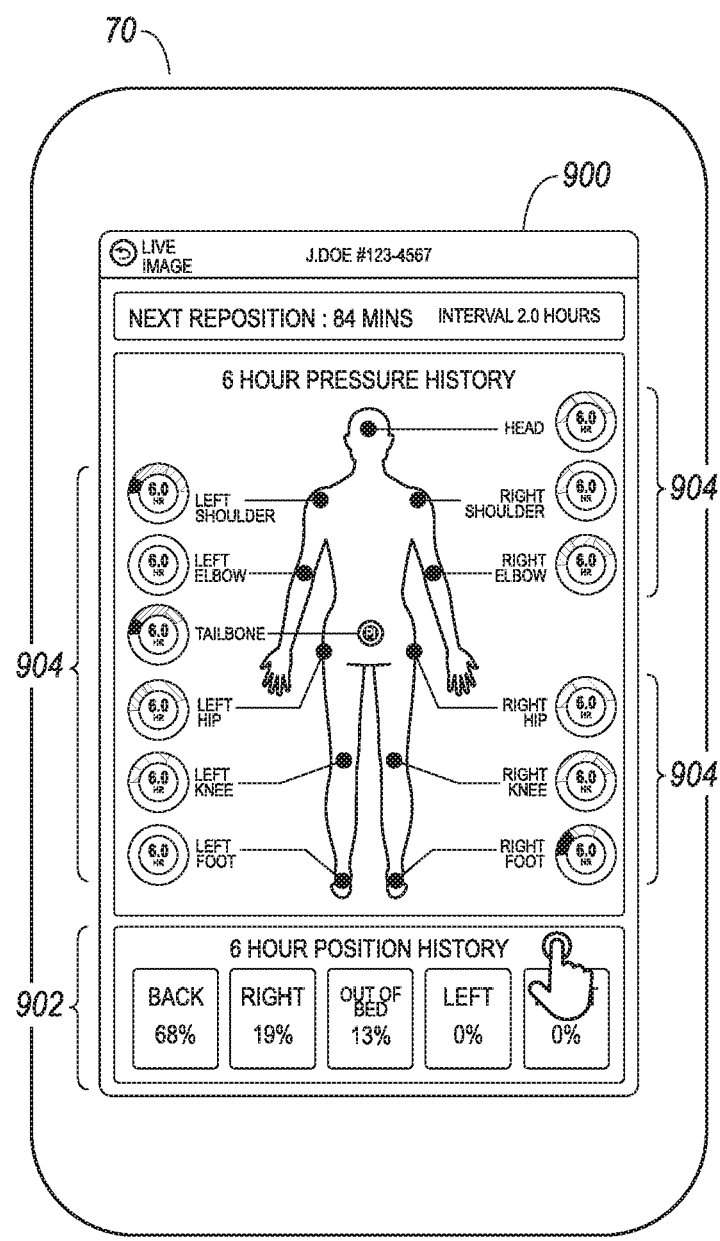
FIG. 9 illustrates a computer user interface of the system including a dashboard for display of body position history represented visually in a lower region of the dashboard and body area pressure history represented as pie charts in a peripheral region of the dashboard.
Figure 15:
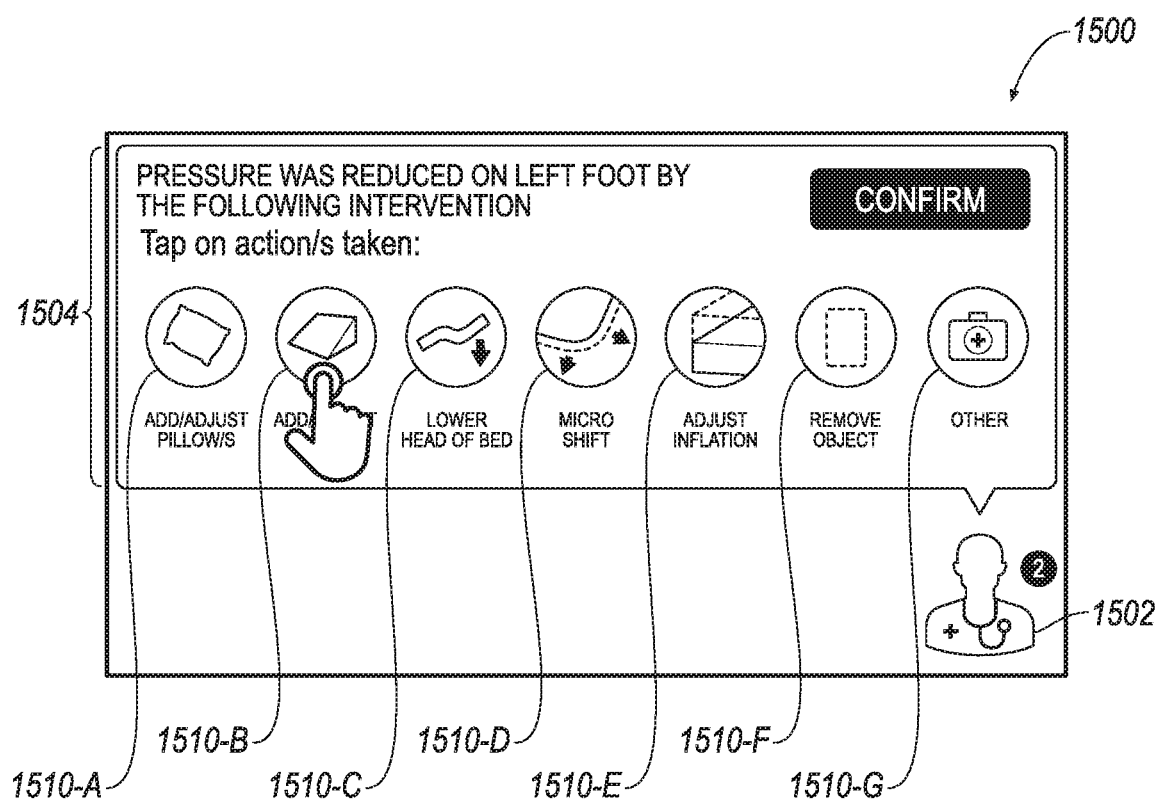
FIG. 15 illustrates a computer user interface of the system for receiving input from a caregiver, for example, as to what intervention was taken to lower pressure in a body area.

The user interface 700 may also include additional controls to allow for navigation to other user interfaces with the system 10. The user interface 700-A may include menu controls 718 and 720. Upon selection of menu control 718, a dashboard user interface (as shown in FIG. 9, for example) may be displayed or a user interface to input intervention information relating to lower pressure in a body area (as shown in FIG. 15, for example). Upon selection of menu control 720, a side bar menu for displaying a menu of various functions of system 10 to be displayed.

Figure 7B:
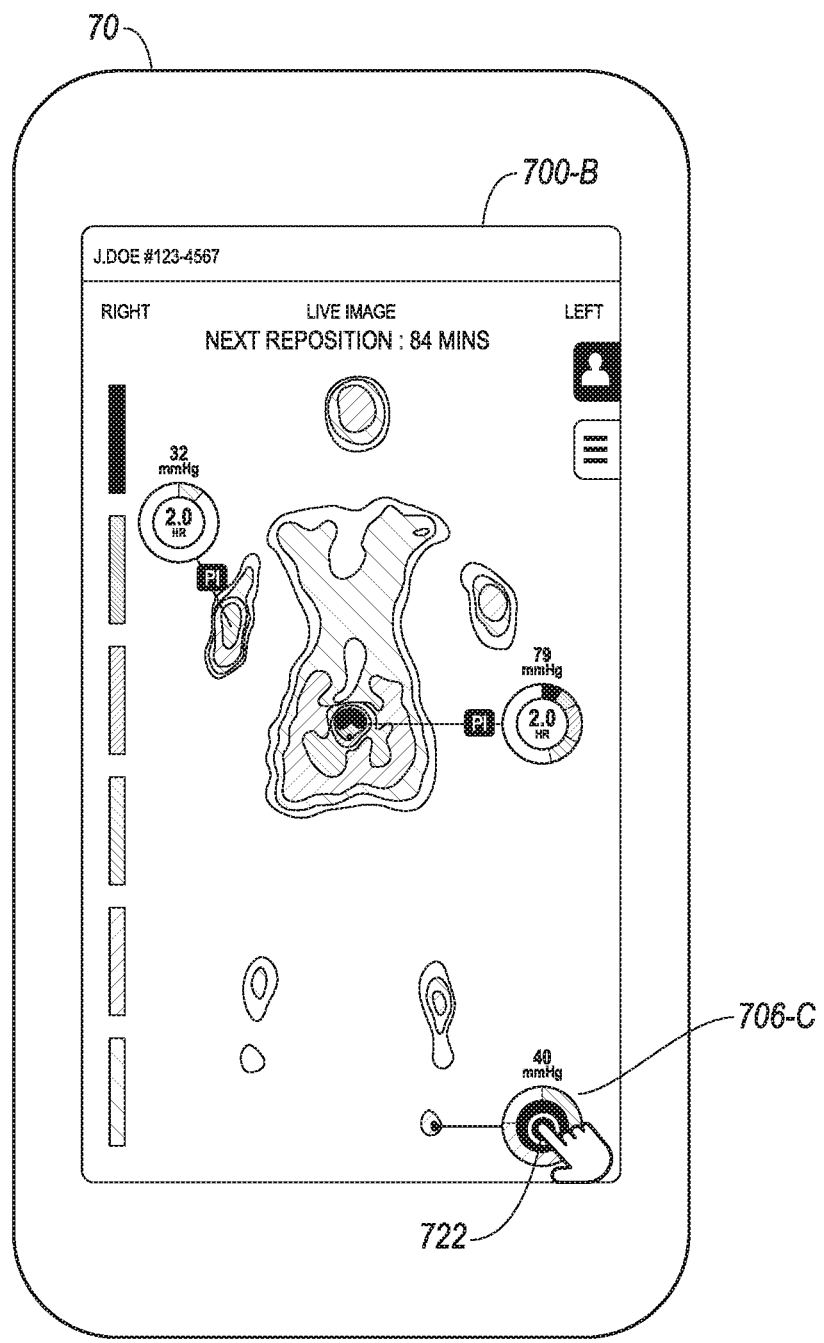
Figure 8:
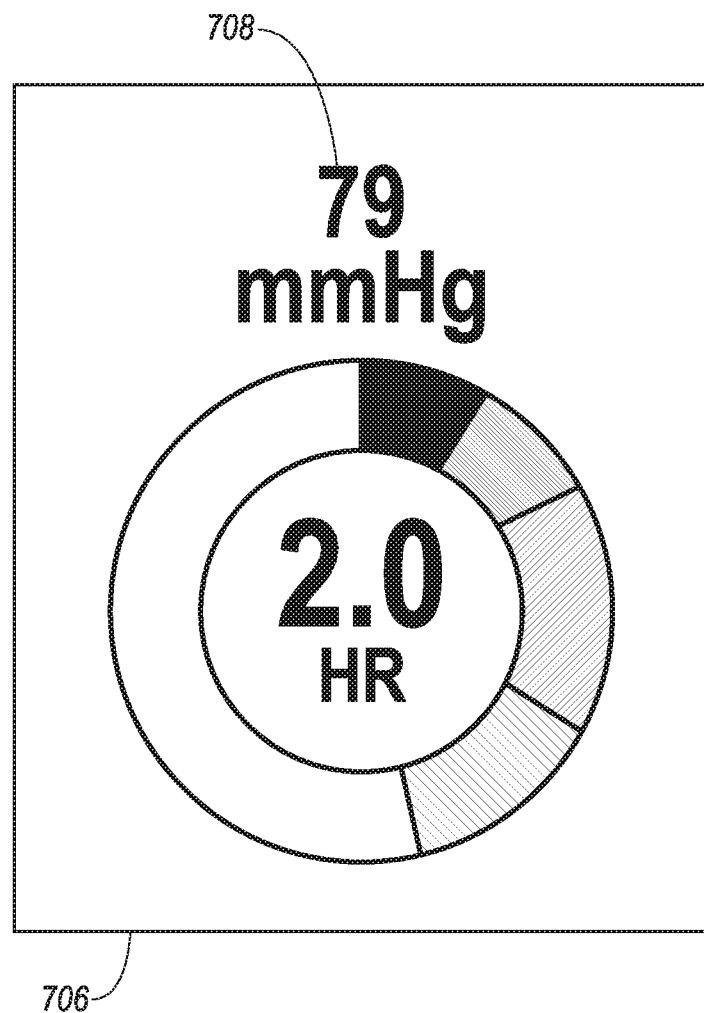
FIG. 8 illustrates a magnified view of a body area pressure history represented as a pie chart.

FIG. 7B depicts body area pressure history indication 706-C for the left heel of the subject. The pie chart of body area pressure history indication 706-C encloses a heel not floated status indicator for the left heel. Although shown for the left heel, the heel not floated status can be displayed for the right heel or both heels. The body area pressure history indication 706-C can be presented to the caregiver via display unit 70. A floated heel may indicate that the subject's heel is positioned in such a way to remove all or most of the pressure to the heel from the support surface, e.g., the mattress. Often, a blanket is on the subject, obscuring the caregiver's view of the heel or heels. In these situations, the caregiver would need to remove the blanket to determine the float status of the heel or heels. According to system 10 and user interface 700-B, a determination is made based on the sensor pressure data 502 using the body position detection algorithm 504 and the pressure determination algorithm 508. If it is determined that the heel(s) are not floated, then the boy area pressure history indication 706-C includes a "not floated" indicator 722. Accordingly, without disturbing the subject, a caregiver can realize whether or not the heel(s) are floated, and take action based on the status. Certain subjects may need their heel(s) floated as much as possible, and all individuals need their heels floated from time to time because it is a leading area of pressure injuries. The "not floated" indicator 722 may be used by a caregiver to determine that the subject should be adjusted to float the heel or heels.

FIG. 9 illustrates a computer user interface 900 of the system including a dashboard for display of body position history represented visually in a lower region of the dashboard and body area pressure history represented as pie charts in a peripheral region of the dashboard. User interface 900 may be presented to the caregiver via the display unit 70, e.g., responsive to the caregiver selecting the menu control 718 of user interface 700-A.

The user interface 900 may include a body position history 902 configured to indicate to the caregiver the relative amounts of time that the subject spent in each of a set of predefined body positions. For instance, as shown the body position history 902 includes indication of the amount of time that the subject spent within each of a number of body positions, e.g., back-side resting body position, a right side resting body position, a stomach or front-side resting body position, an out of bed position, or a left side resting body position. The body position history 902 indicates that the subject was on his/her back 68% of the time, on his/her right side 19% of the time, on his/her left side 0% of the time, on his/her front side 0% of the time, and out of the bed 13% of the time. A body area pressure history 904 indicates pressure of individual body areas over time in a pie chart representation. As shown below in FIG. 11, body area pressure history is represented in a vertical chart as opposed to a pie chart representation as depicted in FIG. 9.

Figure 10:
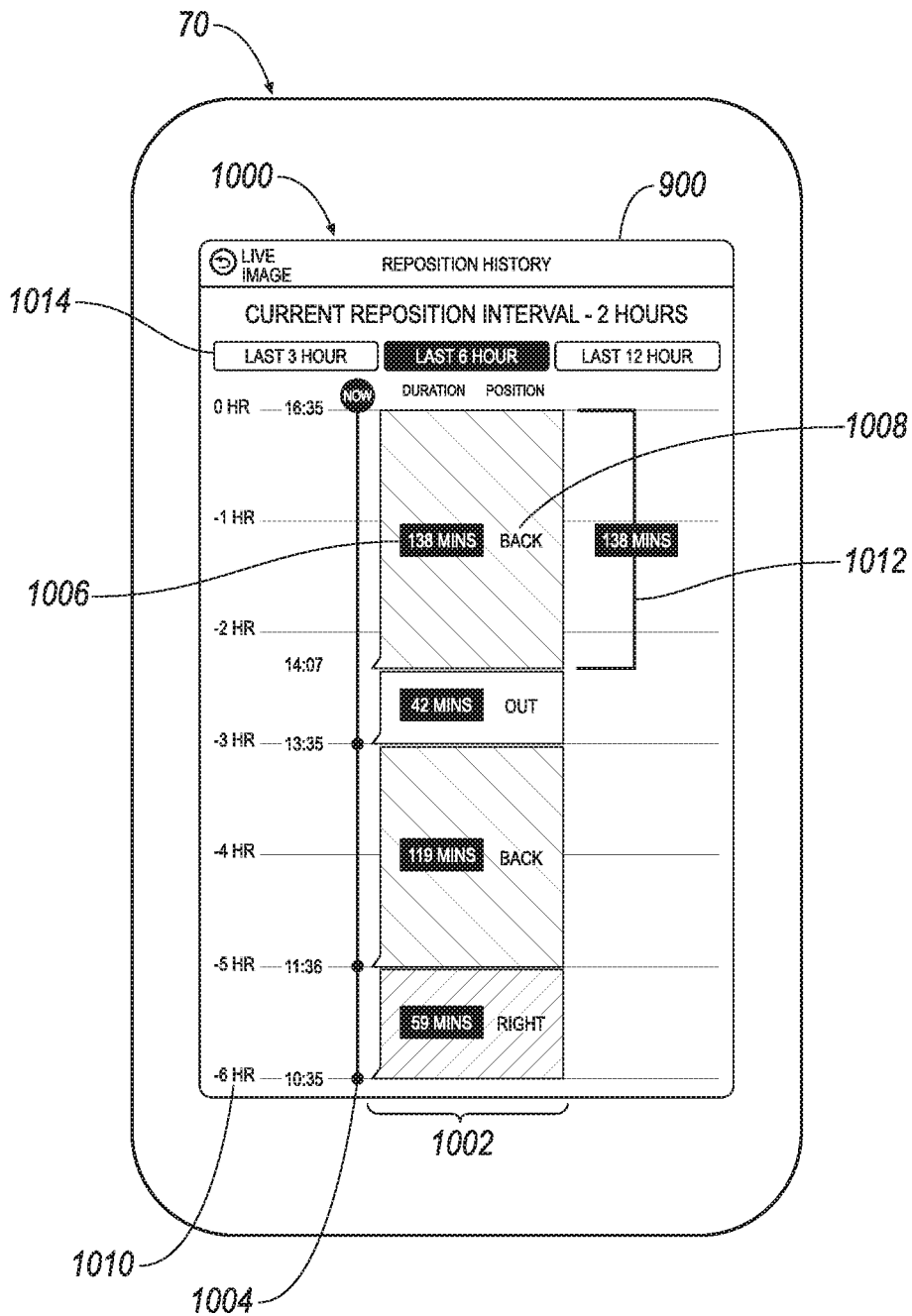
FIG. 10 illustrates a computer user interface of the system for displaying body reposition history represented as a vertical chart.

The user interface 1000 of FIG. 10 may include a body reposition history 1002 in a vertical chart configured to present information indicative of the body position 504 of the subject over the last six (6) hours, although other periods of time, such as three (3) and twelve (12) hours are contemplated. The user interface 1000 includes a body reposition history timeline 1004 to identify the timing of each period of body position and each reposition between two successive body positions. Each period of body position also includes an indication 1006 of total time in that body position and an indication 1008 of the body position. At 1010, a time scale is provided for showing the elapsed time within the relevant period of time, e.g., six (6) hours as shown in FIG. 10. At 1012, the user interface 1000 identifies and highlights when reposition has not taken place within the prescribed period of time or interval, e.g., two (2) hours as shown in FIG. 10. The user interface 1000 may also include additional features, such as time period controls 1014 that, when selected, causes the body reposition history 1002 to be displayed for the identified time period.

Figure 11:
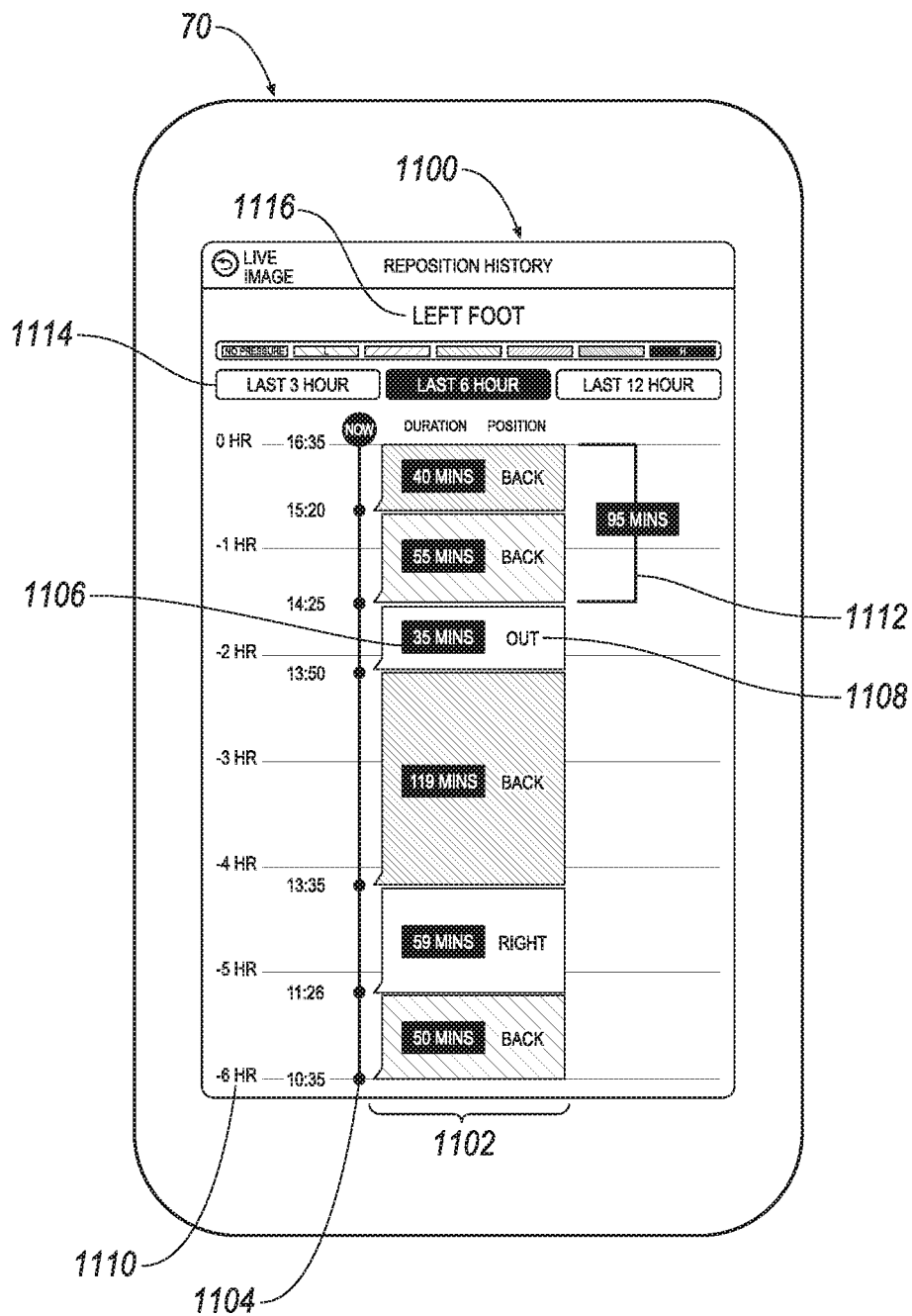
FIG. 11 illustrates a computer user interface of the system for displaying body area pressure history represented as a vertical chart.

FIG. 11 illustrates a user interface 1100 of the system 10 for displaying body area pressure history represented as a vertical chart. In an example, the user interface 1100 may be presented to the caregiver via the display unit 70, e.g., responsive to the caregiver selecting an observed body area of the user interface 700A, for example. The body area pressure history can be shown in the selected reposition history period, or if no reposition history period is selected, the default is two (2) hours, or the pressure history of all body areas can be shown on a dashboard, as shown in FIG. 9. User interface 1100 includes body area pressure history 1102 configured to present information indicative of the body position 504 of the subject over the last six (6) hours, although other periods of time, such as three (3) and twelve (12) hours are contemplated. The body area pressure history 1102 includes a body area pressure history and body reposition history timeline 1104 to identify the timing of each period of body position and each reposition between two successive body positions. Each period of body position also includes an indication 1106 of total time in that body position and an indication 1108 of the body position, and the pressure category, level or range. At 1110, a time scale is provided for showing the elapsed time within the relevant period of time, e.g., six (6) hours as shown in FIG. 11. At 1112, the user interface 1100 identifies and highlights when reposition has not taken place within the prescribed period of time or interval. Thus, the body area pressure history 1102 may be used to allow a caretaker to visually review both subject body position and body area pressure at a specific body area. The user interface 1100 may also include additional features, such as a time period control 1114 that, when selected, causes the body area pressure history 1102 to be displayed for the identified time period. The user interface 1100 may also include a label 1116 indicating that the display is of the body area pressure history for the selected body area of the subject.

Figure 12:
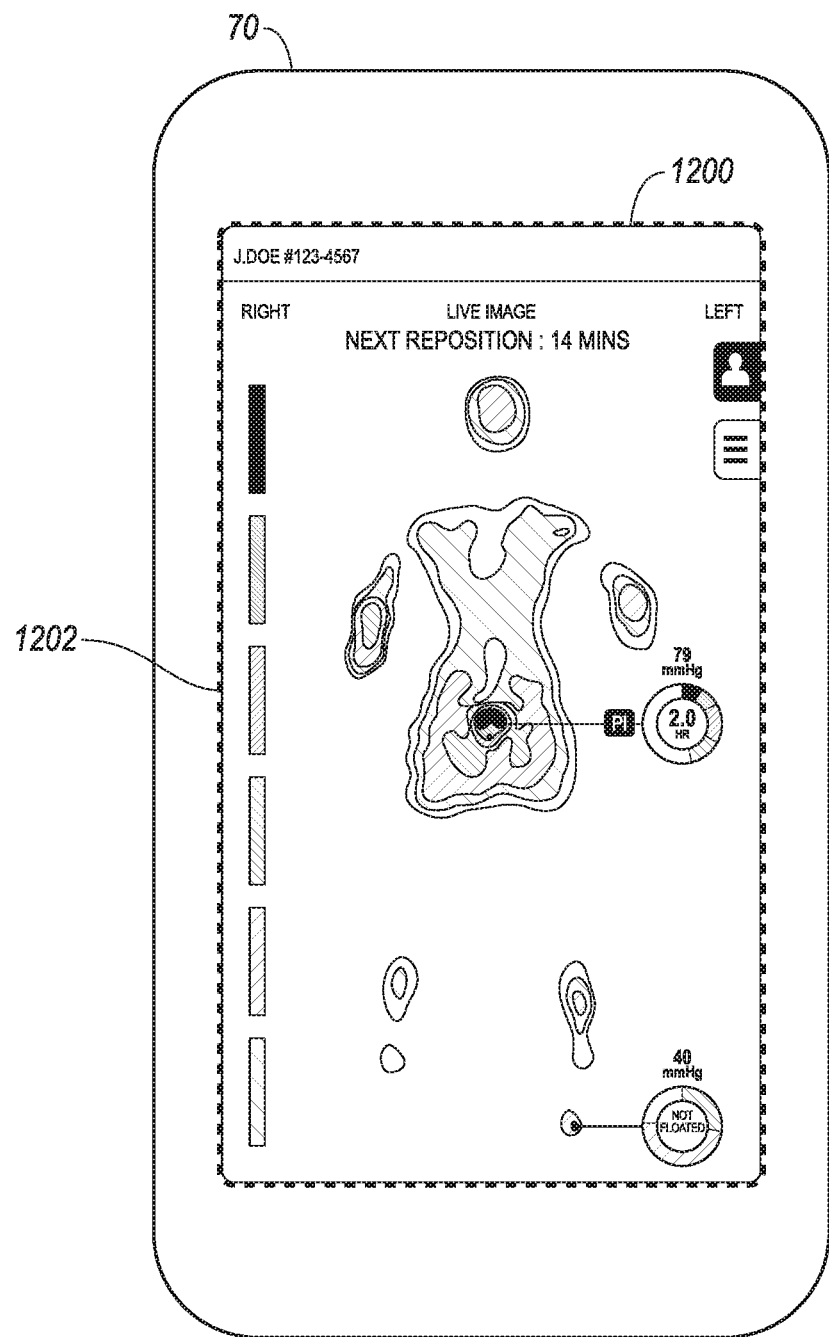
FIG. 12 illustrates a computer user interface of the system for indicating that the reposition timer has identified an upcoming reposition event of the subject.

FIG. 12 illustrates a user interface 1200 of the system 10 for indicating that the reposition timer 716 identifies an upcoming reposition event of the subject. In an example, the user interface 1200 may be presented to the caregiver via the display unit 70, e.g., responsive to the system determining that the reposition timer 716 has reached below a predetermined time threshold, e.g., fifteen (15) minutes. The reposition timer 716 may count down so long as the body position 506 remains consistent, but may reset back to the value of a timer interval control, e.g., two (2) hours, responsive to a change in the body position 506. For instance, the reposition timer 716 may reset responsive to determination that the subject is in a new position for a predefined period of time, such as in a new position for at least one (1) minute.

Responsive to the reposition timer 716 falling below the threshold value, the system 10 may display a reposition alert 1202 on the user interface 1200. In an example, the reposition alert 1202 may be configured to display in a conspicuous manner, e.g., pulse in yellow, to draw the attention of a caretaker. The reposition alert 1202 may automatically dismiss responsive to a change in the body position 506. In other embodiments, the alert 1202 may be an audible alert or an alert transmitted to a caregiver's station or caregiver directly.

Figure 13:
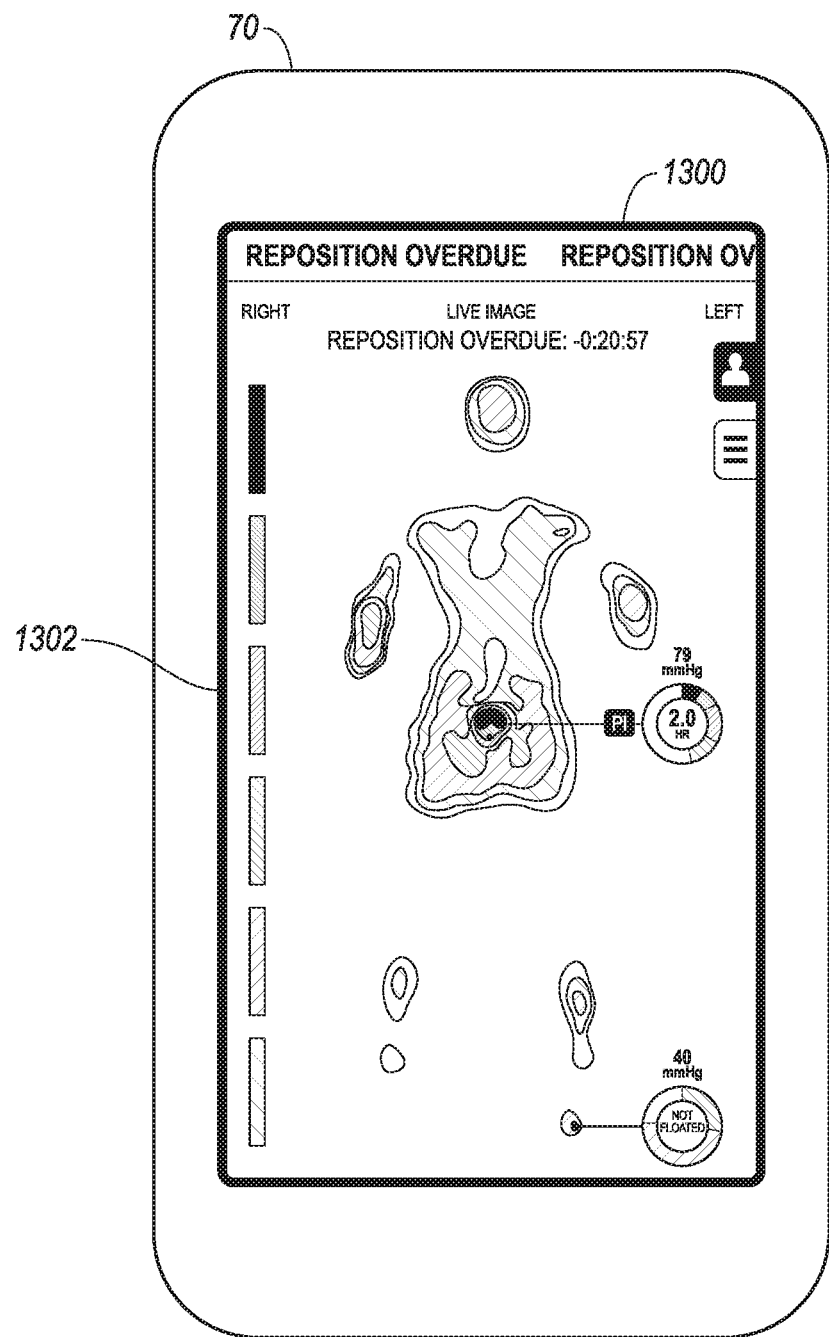
FIG. 13 illustrates a computer user interface of the system for indicating that the reposition timer has identified a past-due reposition event of the subject.

FIG. 13 illustrates a user interface 1300 of the system 10 for indicating that the reposition timer 716 identifies a past-due reposition event of the subject. In an example, the user interface 1300 may be presented to the caregiver via the display unit 70, e.g., responsive to the system determining that the reposition timer 716 has expired. For instance, if no change in body position 506 is detected despite display of the reposition alert 1302, the system may transition to display of the reposition warning 1302. In an example, the reposition warning 1302 may be configured to display in a conspicuous manner, e.g., pulse in red and sound an alarm, to draw the attention of a caretaker. The reposition warning 1302 may automatically dismiss responsive to a change in the body position 506 for the predetermined period of time as discussed above. In other embodiments, the warning 1302 may be an audible alert or an alert transmitted to a caregiver's station or caregiver directly.

Figure 14:
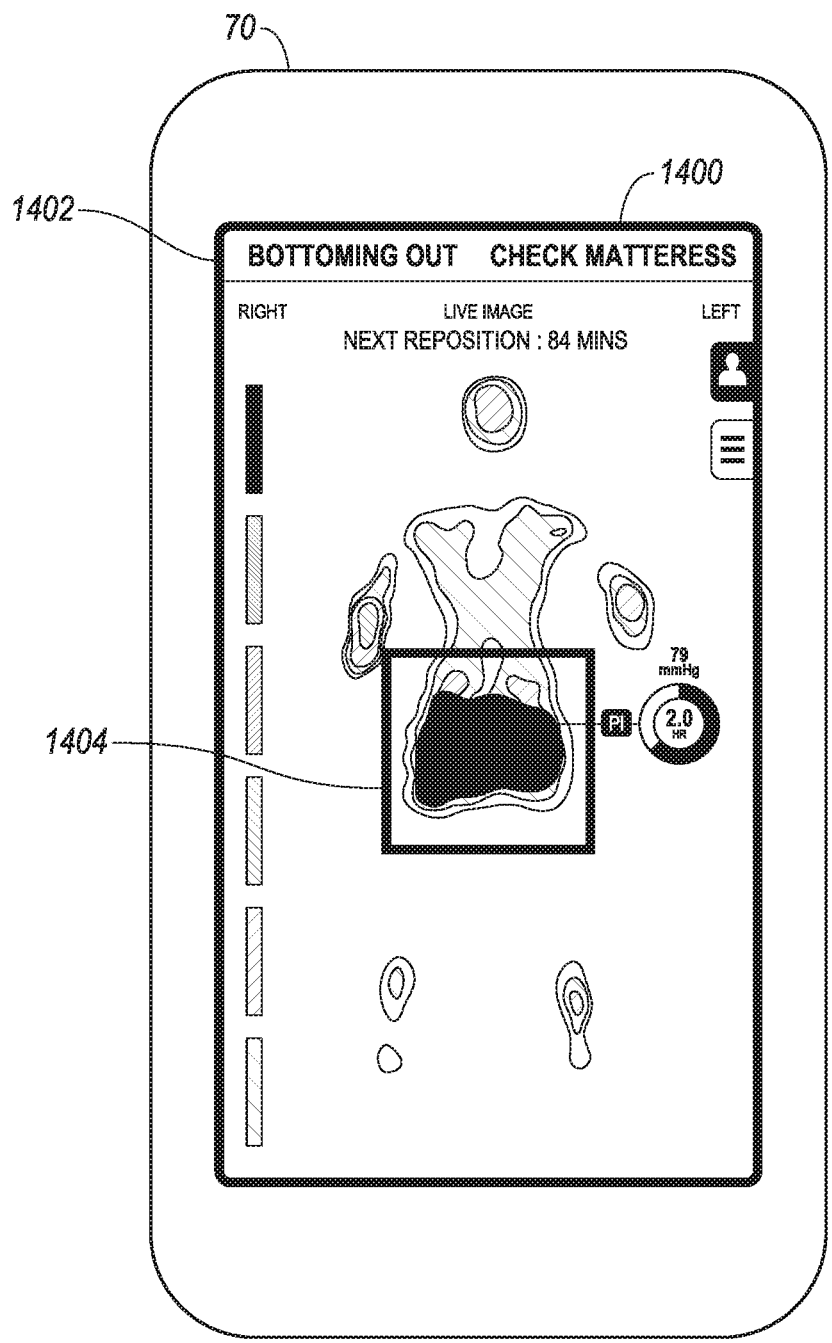
FIG. 14 illustrates a computer user interface of the system for indicating situations in which the subject has bottomed out so that the subject is lying on a bed frame situated under the pressure detection sheet and mattress.

FIG. 14 illustrates an example user interface 1400 of the system 10 for indicating situations in which the sensors 32 of the pressure detection device 30 indicate that the subject has bottomed out so that the subject is lying on the bed frame situated under the pressure detection sheet and mattress. In an example, the user interface 1400 may be presented to the caregiver via the display unit 70, e.g., responsive to the system determining that the pressure for a region of the pressure-detection device 30 consistently reads a value indicative of full pressure across a large area, such as the sacral body region as this is where a large concentration of weight resides, especially if the head of the bed is elevated. This may occur for many reasons, e.g., a traditional foam mattress has deteriorated in the sacral body region due to too long of use, or in the case of air beds where the bed is under-inflated. The user interface 1400 may include a bottoming-out warning indication 1402 that the bottoming out condition is detected, as well as a bottomed-out area warning indication 1404 around the area of full pressure triggering the warning to occur. In an example, the bottoming out warning indication 1404 and bottomed-out area warning indication 1404 may be configured to display in a conspicuous manner, e.g., pulsing in red and/or sounding an alarm, to draw the attention of a caretaker.

FIG. 15 illustrates user interface 1500 of the system 10 for receiving input from a caregiver as to what intervention was taken to lower pressure in a body area. The user interface 1500 may be presented to the caregiver via the display unit 70, e.g., responsive to the system 10 determining that intervention was taken to lower pressure in a body area.

As shown in FIG. 15, the notification indication 1502 indicates that there are two pending notifications for the caregiver. Details of one of the pending notifications is displayed to the user in the balloon indication 1504, e.g., responsive to the caregiver selecting the notification indication 1502. By using the notification indication 1502, the system 10 may accordingly provide notifications to the caregiver that may be answered when convenient, without obscuring or otherwise taking over the user interface of the display unit 70 when the notifications are not being addressed.

As shown in the balloon indication 1504, the notification includes a description 1506 indicating that pressure was reduced on one of the body area of the subject (in this example, the left foot). The user interface 1500 also includes a graphical indication 1508 associated with the location of the pressure representation 702 where the pressure was reduced. As shown, the intervention controls 1510 may include: an add/adjust pillow intervention control 1510-A that may be selected to indicate that a pillow was used to address a high pressure situation, an add/adjust wedges intervention control 1510-B that may be selected to indicate that a wedge was used to address a high pressure situation, a lower head of bed intervention control 1510-C that may be selected to indicate that the head of the bed was lowered to address a high pressure situation, a microshifting intervention control 1510-D that may be selected to indicate that microshifting was performed to address a high pressure situation, an adjust-inflation intervention control 1510-E that may be selected to indicate that settings of the air bed were adjusted to address a high pressure situation, an object-removed intervention control 1510-F that may be selected to indicate that a wedge, pillow or other object was removed to address high pressure situation, and an "other" intervention control 1510-G that may be selected to allow for text or voice entry of a description of an action that was performed that is not listed by the other intervention controls 1510.

Thus, the system 10 may save the received action information in connection with data regarding the lowering of pressure in a body area, such that when similar situations occur in the future, the system may present to the caregiver information regarding the actions that were indicated as being performed to address the situations in the past.

Figure 16:
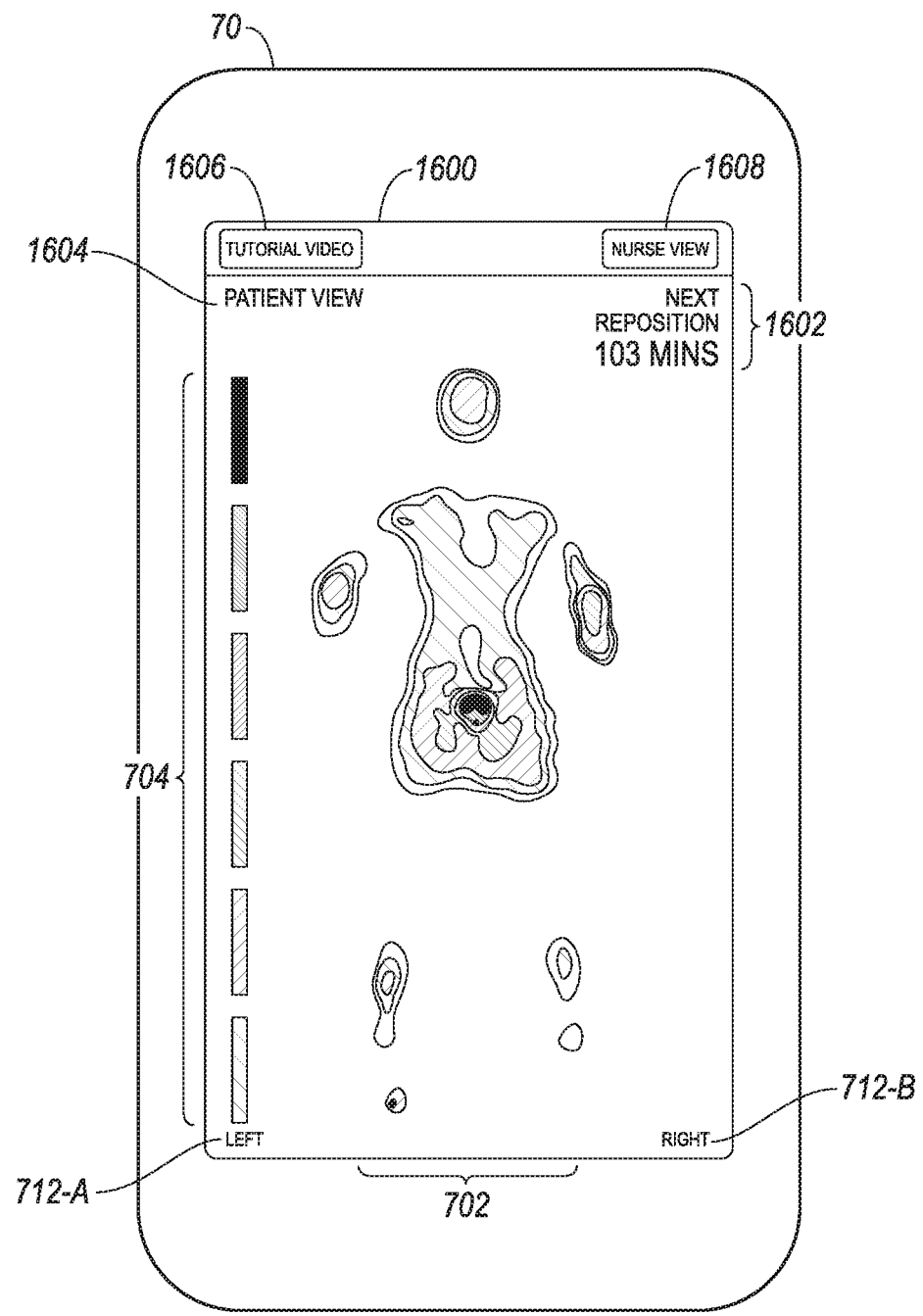
FIG. 16 illustrates a computer user interface of a patient view to be presented to the subject, or other individuals present, such as friends and family, instead of to the caregiver.

FIG. 16 illustrates user interface 1600 of a patient view to be presented to the subject, family or friend, instead of to the caregiver. In an example, the display unit 70 may present the patient view when the display unit 70 has not been interacted with by a caregiver for a predefined timeout period of time (e.g., five minutes, etc.). As opposed to the user interfaces discussed above (referred to sometimes as nurse or caregiver views), the patient view user interface 1600 is designed to give information suitable for viewing by the subject (e.g., an enlarged view of the pressure representation), but without display of patent details or details relating to the condition of the patient.

In the illustrated example interface 1600, the patient view includes the body area pressure representation 702 of the subject and the legend 704 indicating the values of the body area pressure history 702. The patient view may also display the reposition timer 1602 indicating when the subject should be moved. However, the patient view does not display the details related to body areas, such as the body area pressure history, peak pressure value indications, body position history, and/or body reposition history timeline 1004, shown in other user interfaces.

The user interface 1600 may also include a patient view label 1604 to indicate to users that the user interface 1600 is for the subject to view, and does not include the additional medical details available in the nurse views. As the user interface 1600 is for patients and not medical caregivers, the user interface 1600 includes a tutorial control 1606 that, when selected, presents a tutorial explaining the functionality of the display unit 70 in a manner appropriate for the subject. The user interface 1600 also includes a nurse view control 1608 that, when selected, transitions the user interface 1600 from the patient view to the nurse view, e.g., from the user interface 1600 to a user interface such as one of the user interfaces 700. In some cases, credentials such as a login/password or biometrics may be required to be provided to the display unit 70 or other system 10 element to transition the user interface back to the nurse/caretaker view.

Figure 17A:
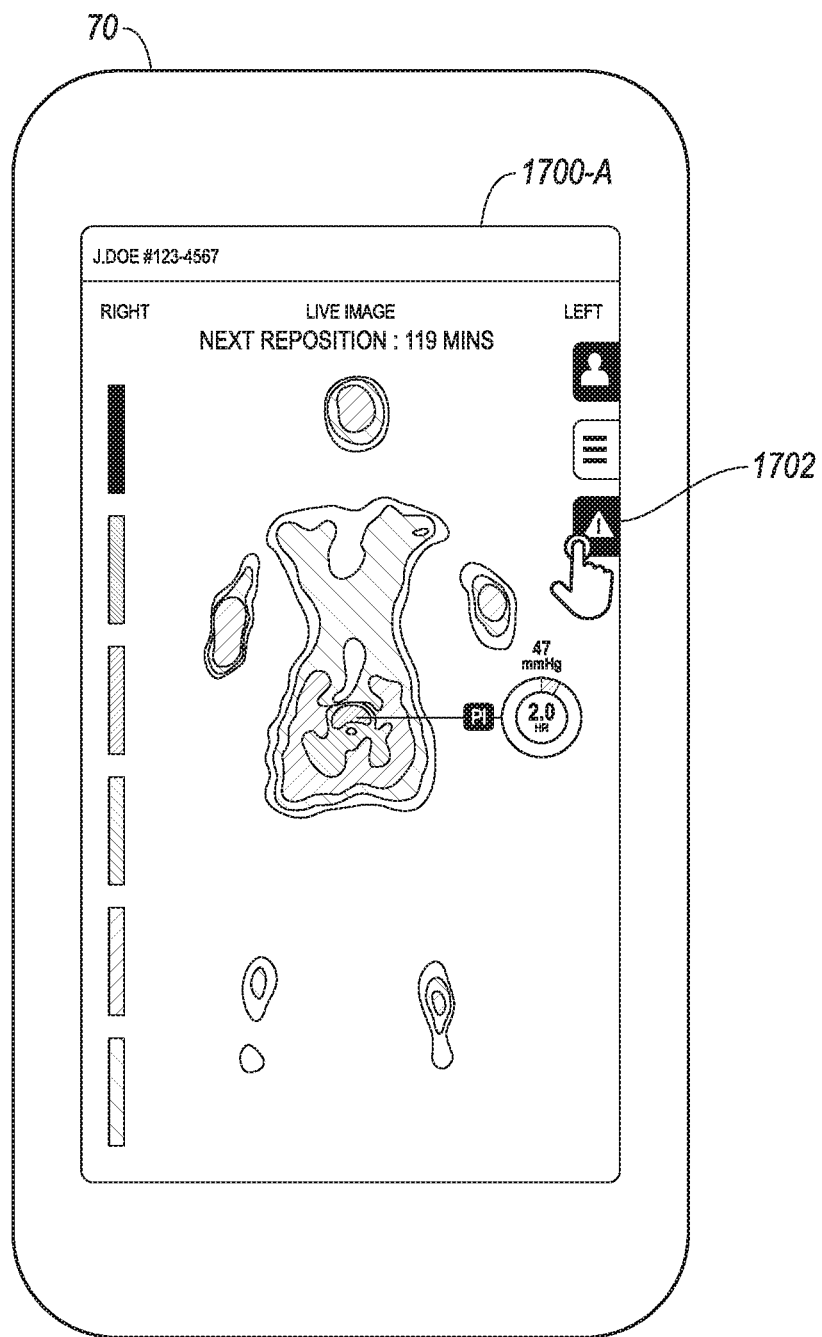
FIGS. 17A, 17B and 17C illustrate computer user interfaces in connection with an alert screen to alert an individual, e.g., a caregiver, of one or more alert incidents.
Figure 17B:
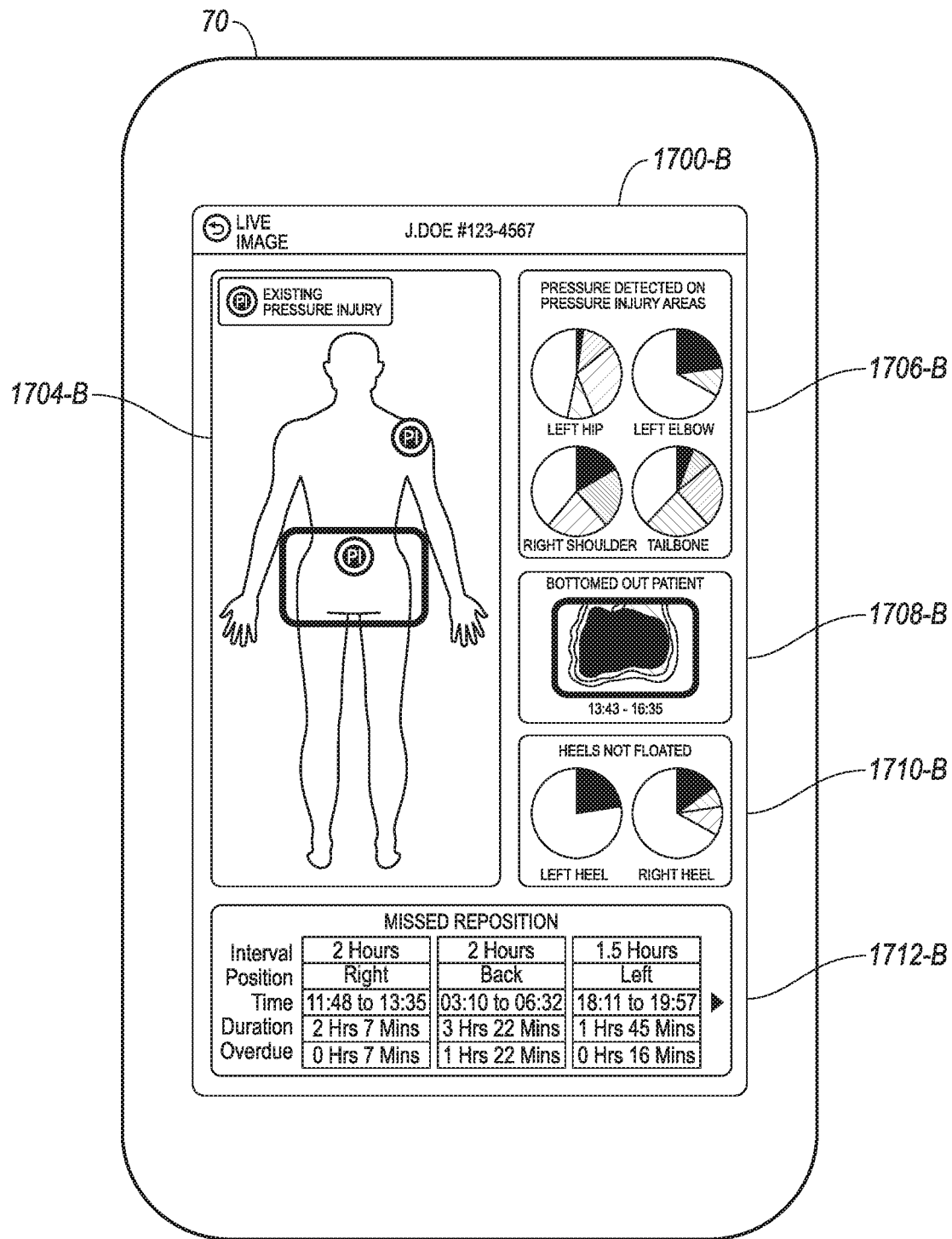
Figure 17C:
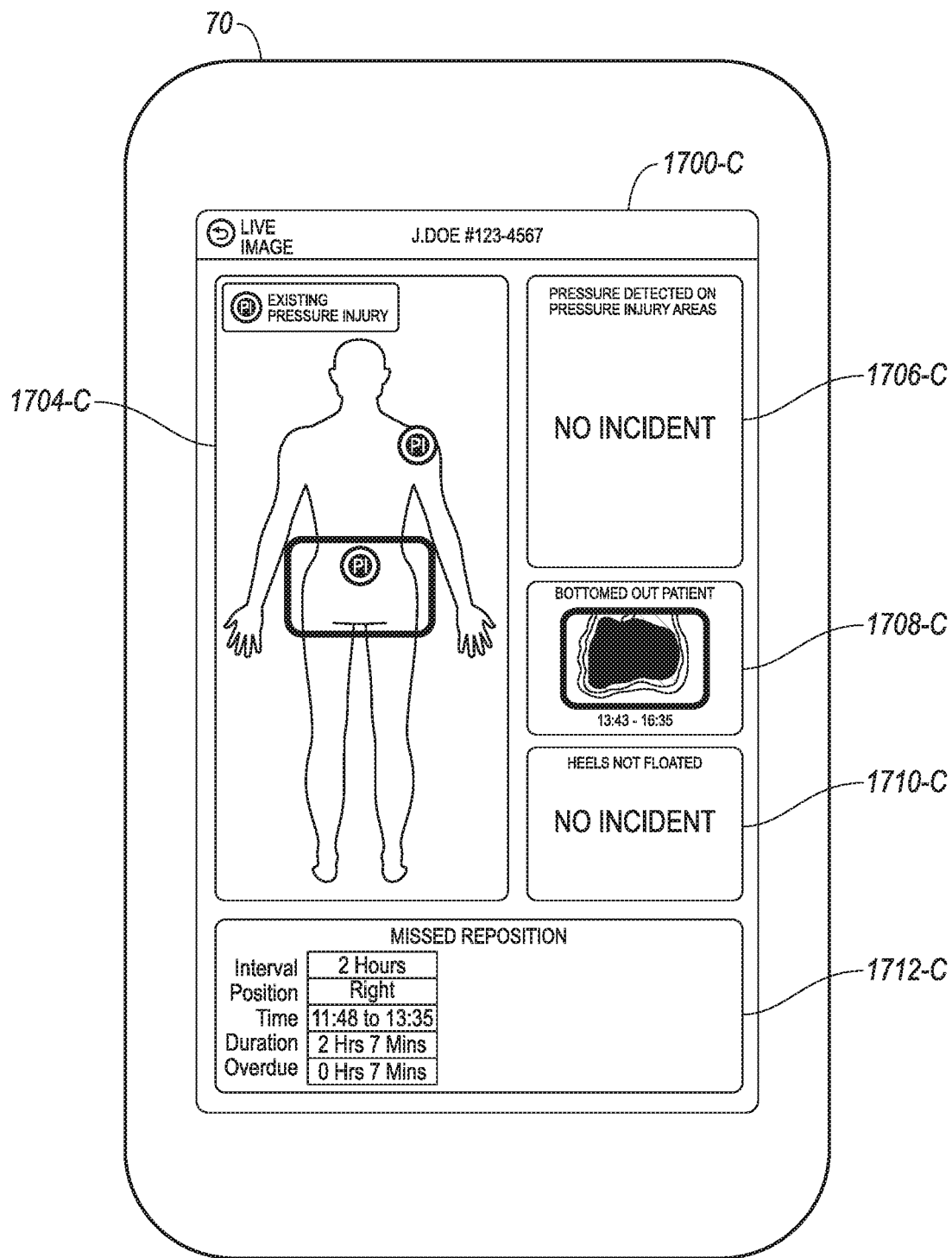

FIGS. 17A, 17B and 17C illustrate computer user interfaces in connection with an alert screen to alert an individual, e.g., a caregiver, of one or more alert incidents. Once informed of the alert incident, the caregiver can take an action to resolve or address the alert incident.

FIG. 17A illustrates a user interface 1700-A of the system 10 for display of live and historical pressure assessment and observation of a subject. The user interface 1700-A may be presented to a caregiver via the display unit 70. User interface 1700-A includes an alert control 1702 for alerting a user that an alert incident has occurred. The alert control 1702 may be selectively displayed while an alert incident is active. The system 10 can include a duration period for each alert incident in which alert control 1702 is displayed. In one embodiment, the duration period is six (6) hours. As described below, the alert control 1702 can be selectively removed from user interface 1700-A once it is selected by the user and the user views an alert incident user interface and/or takes corrective action determined by the system 10 or through user input. Once the user selects alert control 1702, an alert incident user interface is displayed.

FIGS. 17B and 17C illustrate examples of user interfaces 1700-B and 1700-C of the system 10 for displaying one or more alert incidents. The user interfaces 1700-B and 1700-C may be presented to a caregiver via the display unit 70. Window 1704 is configured to display one or more body areas that currently have a pressure injury for reference by the caregiver. Each user interface 1700-B and 1700-C includes a number of windows 1706 through 1712 in which each window is configured to display a current alert incident or indicate that no such incident is currently active. Window 1706 is configured to display an alert when pressure is currently detected on one or more body areas experiencing a pressure injury. Window 1708 is configured to display an alert when a patient has bottomed out, as described above. Window 1710 is configured to display an alert when the left and/or right heels are not floated, as described above. Window 1712 is configured to display an alert when one or more scheduled repositions have been missed. These alert incidents provide specific information to a caregiver to take immediate corrective action to address the alert incident.

This application is related to U.S. application Ser. No. 15/343,747 filed Nov. 4, 2016, and is herein incorporated by reference in its entirety.

In general, computing systems and/or devices may employ any of a number of computer operating systems, including, but by no means limited to, versions and/or varieties of the Microsoft Windows™ operating system, the Unix operating system (e.g., the Solaris™ operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., the BlackBerry OS distributed by Research In Motion of Waterloo, Canada, and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java.™, C, C#, C++, Visual Basic, Java Script, Perl, etc. In general, a processor or microprocessor receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire, and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories, or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may include such instructions stored on computer readable media for carrying out the functions described herein. Such instructions may be provided as software that when executed by the processor provides the operations described herein. Alternatively, the instructions may be provided as hardware or firmware, or combinations of software, hardware, and/or firmware.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system comprising:
 a computer communicatively coupled to a pressure sensor device to periodically receive pressure sensor data experienced by a subject at locations on the pressure sensor device and having non-transitory memory for storing machine instructions that are to be executed by the computer, the machine instructions when executed by the computer implement the following functions:

receive an input of an intervention action, the input and intervention action being received during a first high-pressure situation at a first time, the intervention action resulting in a pressure lowering of a body area of the subject to end the first high-pressure situation, the first high-pressure situation comprises a first time period, and the first time is during the first time period; and responsive to determining a second high-pressure situation at the body area of the subject at a second time later than the first time, display the intervention action during the second high-pressure situation, the intervention action resulting in a second pressure lowering of the body area of the subject to end the second high-pressure situation, the second high-pressure situation comprises a second time period, and the second time is during the second time period.

2. The system of claim 1, wherein the machine instructions when executed by the computer implement the following function: prompt for the input of the intervention action upon detecting the pressure lowering of the body area of the subject to end the first high-pressure situation.

3. The system of claim 2, wherein the input of the intervention action is received from a caregiver, the subject or an individual associated with the subject.

4. The system of claim 1, wherein the machine instructions when executed by the computer implement the following function: prompt for the input of the intervention action upon detecting the intervention action resulting in the pressure lowering of the body area of the subject to end the first high-pressure situation.

5. The system of claim 4, wherein the input of the intervention action is received from a caregiver, the subject or an individual associated with the subject.

6. The system of claim 1, wherein the machine instructions when executed by the computer implement the following function: detect the intervention action during the first high-pressure situation.

7. The system of claim 1, wherein the intervention action is a subject movement, adjustment or readjustment.

8. The system of claim 1, wherein the machine instructions when executed by the computer implement the following function: detect a reduction in pressure on the body area to end the first high-pressure situation without a corresponding change in a body position of the subject.

9. The system of claim 1, wherein the intervention action is selected from a user interface.

10. The system of claim 1, wherein the machine instructions when executed by the computer implement the following function: store the intervention action as a historical record of the subject.

11. A non-transitory computer-readable medium having computer-readable instructions stored thereon that are configured to be executed by a computer to:

receive an input of an intervention action, the input and intervention action being received during a first high-pressure situation at a first time, the intervention action resulting in a pressure lowering of a body area of a subject to end the first high-pressure situation, the first high-pressure situation comprises a first time period, and the first time is during the first time period; and responsive to determining a second high-pressure situation at the body area of the subject at a second time later than the first time, display the intervention action during the second high-pressure situation, the intervention action resulting in a second pressure lowering of the body area of the subject to end the second high-pressure situation, the second high-pressure situation comprises a second time period, and the second time is during the second time period.

12. The non-transitory computer-readable medium of claim 11, wherein the computer-readable instructions are further configured to be executed by the computer to prompt for the input of the intervention action upon detecting the pressure lowering of the body area of a subject to end the first high-pressure situation.

13. The non-transitory computer-readable medium of claim 11, wherein the computer-readable instructions are further configured to be executed by the computer to prompt for the input upon detecting the intervention action resulting in the pressure lowering of the body area of a subject to end the first high-pressure situation.

14. The non-transitory computer-readable medium of claim 11, wherein the computer-readable instructions are further configured to be executed by the computer to detect the intervention action during the first high-pressure situation.

15. The non-transitory computer-readable medium of claim 11, wherein the intervention action is a subject movement, adjustment or readjustment.

16. The non-transitory computer-readable medium of claim 11, wherein the computer-readable instructions are further configured to be executed by the computer to detect a reduction in pressure on the body area to end the first high-pressure situation without a corresponding change in a body position of the subject.

17. The non-transitory computer-readable medium of claim 11, wherein the intervention action is selected from a user interface.

18. The non-transitory computer-readable medium of claim 11, wherein the computer-readable instructions are further configured to be executed by the computer to store the intervention action as a historical record of the subject.

19. A method comprising:

receiving an input of an intervention action, the input and intervention action being received during a first high-pressure situation at a first time, the intervention action resulting in a pressure lowering of a body area of a subject to end the first high-pressure situation, the first high-pressure situation comprises a first time period, and the first time is during the first time period; and responsive to determining a second high-pressure situation at the body area of the subject at a second time later than the first time, displaying the intervention action during the second high-pressure situation, the intervention action resulting in a second pressure lowering of the body area of the subject to end the second high-pressure situation, the second high-pressure situation comprises a second time period, and the second time is during the second time period.

20. The method of claim 19, further comprising detecting the intervention action during the first high-pressure situation.

21. The method of claim 20, further comprising prompting for the input of the intervention action upon detecting the intervention action.

22. The method of claim 19, wherein the intervention action is a reduction in pressure on the body area to end the first high-pressure situation without a corresponding change in a body position of the subject.

23. The method of claim 22, further comprising prompting for the input of the intervention action upon detecting the reduction in pressure.

\* \* \* \* \*